United States Patent
Sidar

(10) Patent No.: US 10,412,290 B2
(45) Date of Patent: Sep. 10, 2019

(54) IMAGE CAPTURE AND VIDEO PROCESSING SYSTEMS AND METHODS FOR MULTIPLE VIEWING ELEMENT ENDOSCOPES

(71) Applicant: EndoChoice, Inc., Alpharetta, GA (US)

(72) Inventor: Itay Sidar, Haifa (IL)

(73) Assignee: EndoChoice, Inc., Alpharetta, GA (US)

(*) Notice: Subject to any disclaimer, the term of this patent is extended or adjusted under 35 U.S.C. 154(b) by 276 days.

(21) Appl. No.: 15/423,802

(22) Filed: Feb. 3, 2017

(65) Prior Publication Data
US 2017/0214832 A1    Jul. 27, 2017

Related U.S. Application Data

(62) Division of application No. 14/603,137, filed on Jan. 22, 2015, now Pat. No. 9,706,908.
(Continued)

(51) Int. Cl.
*A61B 1/00* (2006.01)
*A61B 1/05* (2006.01)
(Continued)

(52) U.S. Cl.
CPC ....... *H04N 5/2258* (2013.01); *A61B 1/00009* (2013.01); *A61B 1/00011* (2013.01);
(Continued)

(58) Field of Classification Search
None
See application file for complete search history.

(56) References Cited

U.S. PATENT DOCUMENTS

| 3,639,714 A | 2/1972 | Fujimoto |
| 3,955,064 A | 5/1976 | Demetrio |

(Continued)

FOREIGN PATENT DOCUMENTS

| CA | 2297986 | 3/1999 |
| CA | 2765559 | 12/2010 |

(Continued)

OTHER PUBLICATIONS

International Search Report for PCT/US14/37004, dated Sep. 25, 2014.
(Continued)

*Primary Examiner* — Dakshesh D Parikh
(74) *Attorney, Agent, or Firm* — Bookoff McAndrews, PLLC

(57) ABSTRACT

A multiple sensor endoscope system and a video processing method, wherein the system includes an endoscope having a plurality of daisy chained image sensors and a central control unit, is described. At least one daisy-chained image sensor includes a sensor array for capturing images and generating video packets from the captured images, a video compression unit configured to compress the video packets, a self-packet buffer configured to store the video packets, a serial-to-parallel de-serializer input unit configured to convert serialized input video packets to parallel data, a chain packet buffer configured to store the video packets received from previous-in-chain image sensors, an arbitration unit configured to interleave the stored video packets, and a serial output unit configured to output serially the interleaved video packets. The central control unit is configured to de-interleave the video packets and regenerate separated images as captured by the plurality of daisy chain image sensors.

13 Claims, 12 Drawing Sheets

Related U.S. Application Data

(60) Provisional application No. 61/948,012, filed on Mar. 4, 2014, provisional application No. 61/930,101, filed on Jan. 22, 2014.

(51) Int. Cl.
*A61B 1/06* (2006.01)
*A61B 1/12* (2006.01)
*A61B 1/045* (2006.01)
*G02B 23/24* (2006.01)
*H04N 5/225* (2006.01)

(52) U.S. Cl.
CPC ...... *A61B 1/00177* (2013.01); *A61B 1/00181* (2013.01); *A61B 1/045* (2013.01); *A61B 1/051* (2013.01); *A61B 1/0615* (2013.01); *A61B 1/0638* (2013.01); *A61B 1/0676* (2013.01); *A61B 1/128* (2013.01); *G02B 23/2423* (2013.01); *G02B 23/2484* (2013.01); *H04N 5/2256* (2013.01); *G02B 23/2461* (2013.01); *H04N 2005/2255* (2013.01)

(56) References Cited

U.S. PATENT DOCUMENTS

| | | |
|---|---|---|
| 4,027,697 A | 6/1977 | Bonney |
| 4,037,588 A | 7/1977 | Heckele |
| 4,084,401 A | 4/1978 | Belardi |
| 4,402,313 A | 9/1983 | Yabe |
| 4,461,282 A | 7/1984 | Ouchi |
| 4,494,549 A | 1/1985 | Namba |
| 4,532,918 A | 8/1985 | Wheeler |
| 4,588,294 A | 5/1986 | Siegmund |
| 4,641,635 A | 2/1987 | Yabe |
| 4,727,859 A | 3/1988 | Lia |
| 4,764,001 A | 8/1988 | Yokota |
| 4,801,792 A | 1/1989 | Yamasita |
| 4,825,850 A | 5/1989 | Opie |
| 4,877,314 A | 10/1989 | Kanamori |
| 4,902,115 A | 2/1990 | Takahashi |
| 4,976,522 A | 12/1990 | Igarashi |
| 4,984,878 A | 1/1991 | Miyano |
| 5,007,406 A | 4/1991 | Takahashi |
| 5,014,685 A | 5/1991 | Takahashi |
| 5,193,525 A | 3/1993 | Silverstein |
| 5,224,929 A | 7/1993 | Remiszewski |
| 5,296,971 A | 3/1994 | Mori |
| 5,359,456 A | 10/1994 | Kikuchi |
| 5,395,329 A | 3/1995 | Fleischhacker |
| 5,447,148 A | 9/1995 | Oneda |
| 5,460,167 A | 10/1995 | Yabe |
| 5,464,007 A | 11/1995 | Krauter |
| 5,475,420 A | 12/1995 | Buchin |
| 5,489,256 A | 2/1996 | Adair |
| 5,518,501 A | 5/1996 | Oneda |
| 5,518,502 A | 5/1996 | Kaplan |
| 5,547,455 A | 8/1996 | McKenna |
| 5,547,457 A | 8/1996 | Tsuyuki |
| 5,575,755 A | 11/1996 | Krauter |
| 5,587,839 A | 12/1996 | Miyano |
| 5,630,782 A | 5/1997 | Adair |
| 5,630,798 A | 5/1997 | Beiser |
| 5,662,588 A | 9/1997 | Iida |
| 5,674,182 A | 10/1997 | Suzuki |
| 5,685,821 A | 11/1997 | Pike |
| 5,685,823 A | 11/1997 | Ito |
| 5,702,347 A | 12/1997 | Yabe |
| 5,707,344 A | 1/1998 | Nakazawa |
| 5,725,474 A | 3/1998 | Yasui |
| 5,725,476 A | 3/1998 | Yasui |
| 5,725,477 A | 3/1998 | Yasui |
| 5,725,478 A | 3/1998 | Saad |
| 5,777,797 A | 7/1998 | Miyano |
| 5,782,751 A | 7/1998 | Matsuno |
| 5,800,341 A | 9/1998 | McKenna |
| 5,810,715 A | 9/1998 | Moriyama |
| 5,810,717 A | 9/1998 | Maeda |
| 5,810,770 A | 9/1998 | Chin |
| 5,830,121 A | 11/1998 | Enomoto |
| 5,836,894 A | 11/1998 | Sarvazyan |
| 5,860,913 A | 1/1999 | Yamaya |
| 5,870,234 A | 2/1999 | Ebbesmeier nee Schitthof |
| 5,916,148 A | 6/1999 | Tsuyuki |
| 5,940,126 A | 8/1999 | Kimura |
| 6,058,109 A | 5/2000 | Lechleider |
| 6,095,970 A | 8/2000 | Hidaka |
| 6,095,971 A | 8/2000 | Takahashi |
| 6,117,068 A | 9/2000 | Gourley |
| 6,181,481 B1 | 1/2001 | Yamamoto |
| 6,196,967 B1 | 3/2001 | Lim |
| 6,261,226 B1 | 7/2001 | McKenna |
| 6,277,064 B1 | 8/2001 | Yoon |
| 6,359,674 B1 | 3/2002 | Horiuchi |
| 6,375,610 B2 | 4/2002 | Verschuur |
| 6,402,738 B1 | 6/2002 | Ouchi |
| 6,419,626 B1 | 7/2002 | Yoon |
| 6,476,851 B1 | 11/2002 | Nakamura |
| 6,520,908 B1 | 2/2003 | Ikeda |
| 6,636,254 B1 | 10/2003 | Onishi |
| 6,638,214 B2 | 10/2003 | Akiba |
| 6,673,012 B2 | 1/2004 | Fujii |
| 6,690,337 B1 | 2/2004 | Mayer, III |
| 6,712,760 B2 | 3/2004 | Sano |
| 6,832,984 B2 | 12/2004 | Stelzer |
| 6,888,119 B2 | 5/2005 | Iizuka |
| 6,997,871 B2 | 2/2006 | Sonnenschein |
| 7,154,378 B1 | 12/2006 | Ertas |
| 7,435,218 B2 | 10/2008 | Krattiger |
| 7,621,869 B2 | 11/2009 | Ratnakar |
| 7,630,148 B1 | 12/2009 | Yang |
| 7,701,650 B2 | 4/2010 | Lin |
| 7,713,246 B2 | 5/2010 | Shia |
| 7,746,572 B2 | 6/2010 | Asami |
| 7,813,047 B2 | 10/2010 | Wang |
| 7,828,725 B2 | 11/2010 | Maruyama |
| 7,918,788 B2 | 4/2011 | Lin |
| 7,927,272 B2 | 4/2011 | Bayer |
| 7,967,745 B2 | 6/2011 | Gilad |
| 7,976,462 B2 | 7/2011 | Wright |
| 8,064,666 B2 | 11/2011 | Bayer |
| 8,182,422 B2 | 5/2012 | Bayer |
| 8,197,399 B2 | 6/2012 | Bayer |
| 8,235,887 B2 | 8/2012 | Bayer |
| 8,262,558 B2 | 9/2012 | Sato |
| 8,287,446 B2 | 10/2012 | Bayer |
| 8,289,381 B2 | 10/2012 | Bayer |
| 8,300,325 B2 | 10/2012 | Katahira |
| 8,310,530 B2 | 11/2012 | Bayer |
| 8,353,860 B2 | 1/2013 | Boulais |
| 8,447,132 B1 | 5/2013 | Galil |
| 8,449,457 B2 | 5/2013 | Aizenfeld |
| 8,460,182 B2 | 6/2013 | Ouyang |
| 8,585,584 B2 | 11/2013 | Ratnakar |
| 8,587,645 B2 | 11/2013 | Bayer |
| 8,672,836 B2 | 3/2014 | Higgins |
| 8,715,168 B2 | 5/2014 | Ratnakar |
| 8,797,392 B2 | 8/2014 | Bayer |
| 8,872,906 B2 | 10/2014 | Bayer |
| 8,926,502 B2 | 1/2015 | Levy |
| 9,044,185 B2 | 6/2015 | Bayer |
| 9,101,266 B2 | 8/2015 | Levi |
| 9,101,268 B2 | 8/2015 | Levy |
| 9,101,287 B2 | 8/2015 | Levy |
| 9,144,664 B2 | 9/2015 | Jacobsen |
| 9,289,110 B2 | 3/2016 | Woolford |
| 9,314,147 B2 | 4/2016 | Levy |
| 9,320,419 B2 | 4/2016 | Kirma |
| 2001/0036322 A1* | 11/2001 | Bloomfield ........... G06T 1/0007 382/276 |
| 2002/0017515 A1 | 2/2002 | Obata |
| 2002/0047897 A1 | 4/2002 | Sugimoto |
| 2002/0087047 A1 | 7/2002 | Remijan |
| 2002/0109771 A1 | 8/2002 | Ledbetter |

(56) References Cited

U.S. PATENT DOCUMENTS

| | | |
|---|---|---|
| 2002/0109774 A1 | 8/2002 | Meron |
| 2002/0161279 A1 | 10/2002 | Luloh |
| 2002/0161281 A1 | 10/2002 | Jaffe |
| 2002/0172498 A1 | 11/2002 | Esenyan |
| 2002/0183591 A1 | 12/2002 | Matsuura |
| 2003/0030918 A1 | 2/2003 | Murayama |
| 2003/0063398 A1 | 4/2003 | Abe |
| 2003/0076411 A1 | 4/2003 | Iida |
| 2003/0083552 A1 | 5/2003 | Remijan |
| 2003/0128893 A1 | 7/2003 | Castorina |
| 2003/0139650 A1 | 7/2003 | Homma |
| 2003/0153897 A1 | 8/2003 | Russo |
| 2003/0158503 A1 | 8/2003 | Matsumoto |
| 2003/0163029 A1 | 8/2003 | Sonnenschein |
| 2004/0015054 A1 | 1/2004 | Hino |
| 2004/0046865 A1 | 3/2004 | Ueno |
| 2004/0061780 A1 | 4/2004 | Huffman |
| 2004/0064019 A1 | 4/2004 | Chang |
| 2004/0077927 A1 | 4/2004 | Ouchi |
| 2004/0106850 A1 | 6/2004 | Yamaya |
| 2004/0133072 A1 | 7/2004 | Kennedy |
| 2004/0138532 A1 | 7/2004 | Glukhovsky |
| 2004/0158129 A1 | 8/2004 | Okada |
| 2004/0160682 A1 | 8/2004 | Miyano |
| 2004/0190159 A1 | 9/2004 | Hasegawa |
| 2004/0249247 A1 | 12/2004 | Iddan |
| 2004/0260151 A1 | 12/2004 | Akiba |
| 2005/0018042 A1 | 1/2005 | Rovegno |
| 2005/0020876 A1 | 1/2005 | Shioda |
| 2005/0038317 A1 | 2/2005 | Ratnakar |
| 2005/0047134 A1 | 3/2005 | Mueller |
| 2005/0057687 A1* | 3/2005 | Irani ............... G06T 3/4069 348/443 |
| 2005/0090709 A1 | 4/2005 | Okada |
| 2005/0096501 A1 | 5/2005 | Stelzer |
| 2005/0119527 A1 | 6/2005 | Banik |
| 2005/0124858 A1 | 6/2005 | Matsuzawa |
| 2005/0222499 A1 | 10/2005 | Banik |
| 2005/0234296 A1 | 10/2005 | Saadat |
| 2005/0234347 A1 | 10/2005 | Yamataka |
| 2005/0251127 A1 | 11/2005 | Brosch |
| 2005/0272975 A1 | 12/2005 | McWeeney |
| 2005/0277808 A1 | 12/2005 | Sonnenschein |
| 2005/0283048 A1 | 12/2005 | Gill |
| 2006/0004257 A1 | 1/2006 | Gilad |
| 2006/0047184 A1 | 3/2006 | Banik |
| 2006/0063976 A1 | 3/2006 | Aizenfeld |
| 2006/0069314 A1 | 3/2006 | Farr |
| 2006/0111613 A1 | 5/2006 | Boutillette |
| 2006/0114986 A1 | 6/2006 | Knapp |
| 2006/0149129 A1 | 7/2006 | Watts |
| 2006/0171693 A1 | 8/2006 | Todd |
| 2006/0173245 A1 | 8/2006 | Todd |
| 2006/0183975 A1 | 8/2006 | Saadat |
| 2006/0184037 A1 | 8/2006 | Ince |
| 2006/0189845 A1 | 8/2006 | Maahs |
| 2006/0215406 A1 | 9/2006 | Thrailkill |
| 2006/0235306 A1 | 10/2006 | Cotter |
| 2006/0252994 A1 | 11/2006 | Ratnakar |
| 2006/0264704 A1 | 11/2006 | Fujimori |
| 2006/0293556 A1 | 12/2006 | Gamer |
| 2007/0015989 A1 | 1/2007 | Desai |
| 2007/0049803 A1 | 3/2007 | Moriyama |
| 2007/0055100 A1 | 3/2007 | Kato |
| 2007/0079029 A1 | 4/2007 | Carlson |
| 2007/0088193 A1 | 4/2007 | Omori |
| 2007/0100206 A1 | 5/2007 | Lin |
| 2007/0106119 A1 | 5/2007 | Hirata |
| 2007/0118015 A1 | 5/2007 | Wendlandt |
| 2007/0142711 A1 | 6/2007 | Bayer |
| 2007/0162095 A1 | 7/2007 | Kimmel |
| 2007/0167681 A1 | 7/2007 | Gill |
| 2007/0177008 A1 | 8/2007 | Bayer |
| 2007/0177009 A1 | 8/2007 | Bayer |
| 2007/0185384 A1 | 8/2007 | Bayer |
| 2007/0188427 A1 | 8/2007 | Lys |
| 2007/0197875 A1 | 8/2007 | Osaka |
| 2007/0203396 A1 | 8/2007 | McCutcheon |
| 2007/0206945 A1 | 9/2007 | DeLorme |
| 2007/0213591 A1 | 9/2007 | Aizenfeld |
| 2007/0229656 A1 | 10/2007 | Khait |
| 2007/0241895 A1 | 10/2007 | Morgan |
| 2007/0244353 A1 | 10/2007 | Larsen |
| 2007/0244354 A1 | 10/2007 | Bayer |
| 2007/0247867 A1 | 10/2007 | Hunter |
| 2007/0249907 A1 | 10/2007 | Boulais |
| 2007/0265492 A1 | 11/2007 | Sonnenschein |
| 2007/0265498 A1 | 11/2007 | Ito |
| 2007/0270642 A1 | 11/2007 | Bayer |
| 2007/0279486 A1 | 12/2007 | Bayer |
| 2007/0286764 A1 | 12/2007 | Noguchi |
| 2007/0293720 A1 | 12/2007 | Bayer |
| 2008/0009673 A1 | 1/2008 | Khachi |
| 2008/0021274 A1 | 1/2008 | Bayer |
| 2008/0025413 A1 | 1/2008 | Apostolopoulos |
| 2008/0036864 A1 | 2/2008 | McCubbrey |
| 2008/0045797 A1 | 2/2008 | Yasushi |
| 2008/0058601 A1 | 3/2008 | Fujimori |
| 2008/0071290 A1 | 3/2008 | Larkin |
| 2008/0091065 A1 | 4/2008 | Oshima |
| 2008/0130108 A1 | 6/2008 | Bayer |
| 2008/0151070 A1 | 6/2008 | Shiozawa |
| 2008/0161646 A1 | 7/2008 | Gomez |
| 2008/0163652 A1 | 7/2008 | Shatskin |
| 2008/0167529 A1 | 7/2008 | Otawara |
| 2008/0177139 A1 | 7/2008 | Courtney |
| 2008/0183034 A1 | 7/2008 | Henkin |
| 2008/0183043 A1 | 7/2008 | Spinnler |
| 2008/0221388 A1 | 7/2008 | Courtney |
| 2008/0246771 A1 | 10/2008 | ONeal |
| 2008/0253686 A1 | 10/2008 | Bayer |
| 2008/0262312 A1 | 10/2008 | Carroll |
| 2008/0275298 A1 | 11/2008 | Ratnakar |
| 2008/0303898 A1 | 12/2008 | Nishimura |
| 2009/0005643 A1 | 1/2009 | Smith |
| 2009/0023998 A1 | 1/2009 | Ratnakar |
| 2009/0030275 A1 | 1/2009 | Nicolaou |
| 2009/0054790 A1 | 2/2009 | Czaniera |
| 2009/0062615 A1 | 3/2009 | Yamaya |
| 2009/0076327 A1 | 3/2009 | Ohki |
| 2009/0082624 A1 | 3/2009 | Joko |
| 2009/0086017 A1 | 4/2009 | Miyano |
| 2009/0135245 A1 | 5/2009 | Luo |
| 2009/0137875 A1 | 5/2009 | Kitagawa |
| 2009/0143647 A1 | 6/2009 | Banju |
| 2009/0147076 A1 | 6/2009 | Ertas |
| 2009/0182917 A1 | 7/2009 | Kim |
| 2009/0209811 A1 | 8/2009 | Higuchi |
| 2009/0213211 A1 | 8/2009 | Bayer |
| 2009/0216084 A1 | 8/2009 | Yamane |
| 2009/0225159 A1 | 9/2009 | Schneider |
| 2009/0231419 A1 | 9/2009 | Bayer |
| 2009/0234183 A1 | 9/2009 | Abe |
| 2009/0253966 A1 | 10/2009 | Ichimura |
| 2009/0287188 A1 | 11/2009 | Golden |
| 2009/0287192 A1 | 11/2009 | Vivenzio |
| 2009/0299144 A1 | 12/2009 | Shigemori |
| 2010/0010309 A1 | 1/2010 | Kitagawa |
| 2010/0016673 A1 | 1/2010 | Bandy |
| 2010/0053312 A1 | 3/2010 | Watanabe |
| 2010/0069713 A1 | 3/2010 | Endo |
| 2010/0073470 A1 | 3/2010 | Takasaki |
| 2010/0073948 A1 | 3/2010 | Stein |
| 2010/0076268 A1 | 3/2010 | Takasugi |
| 2010/0123950 A1 | 5/2010 | Fujiwara |
| 2010/0130822 A1 | 5/2010 | Katayama |
| 2010/0141763 A1 | 6/2010 | Itoh |
| 2010/0160729 A1 | 6/2010 | Smith |
| 2010/0174144 A1 | 7/2010 | Hsu |
| 2010/0231702 A1 | 9/2010 | Tsujimura |
| 2010/0245653 A1 | 9/2010 | Bodor |
| 2010/0249513 A1 | 9/2010 | Tydlaska |
| 2010/0280322 A1 | 11/2010 | Mizuyoshi |
| 2010/0296178 A1 | 11/2010 | Genet |

(56) References Cited

U.S. PATENT DOCUMENTS

| | | |
|---|---|---|
| 2010/0326703 A1 | 12/2010 | Gilad |
| 2011/0004058 A1 | 1/2011 | Oneda |
| 2011/0004059 A1 | 1/2011 | Arneson |
| 2011/0034769 A1 | 2/2011 | Adair |
| 2011/0063427 A1 | 3/2011 | Fengler |
| 2011/0084835 A1 | 4/2011 | Whitehouse |
| 2011/0140003 A1 | 6/2011 | Beck |
| 2011/0160530 A1 | 6/2011 | Ratnakar |
| 2011/0160535 A1 | 6/2011 | Bayer |
| 2011/0169931 A1 | 7/2011 | Pascal |
| 2011/0184243 A1 | 7/2011 | Wright |
| 2011/0211267 A1 | 9/2011 | Takato |
| 2011/0254937 A1 | 10/2011 | Yoshino |
| 2011/0263938 A1 | 10/2011 | Levy |
| 2011/0282144 A1 | 11/2011 | Gettman |
| 2011/0292258 A1 | 12/2011 | Adler |
| 2012/0040305 A1 | 2/2012 | Karazivan |
| 2012/0050606 A1 | 3/2012 | Debevec |
| 2012/0053407 A1 | 3/2012 | Levy |
| 2012/0057251 A1 | 3/2012 | Takato |
| 2012/0065468 A1 | 3/2012 | Levy |
| 2012/0076425 A1 | 3/2012 | Brandt |
| 2012/0162402 A1 | 6/2012 | Amano |
| 2012/0200683 A1 | 8/2012 | Oshima |
| 2012/0209071 A1 | 8/2012 | Bayer |
| 2012/0209289 A1 | 8/2012 | Duque |
| 2012/0212630 A1 | 8/2012 | Pryor |
| 2012/0220832 A1 | 8/2012 | Nakade |
| 2012/0224026 A1 | 9/2012 | Bayer |
| 2012/0229615 A1 | 9/2012 | Kirma |
| 2012/0232340 A1 | 9/2012 | Levy |
| 2012/0232343 A1 | 9/2012 | Levy |
| 2012/0253121 A1 | 10/2012 | Kitano |
| 2012/0277535 A1 | 11/2012 | Hoshino |
| 2012/0281536 A1 | 11/2012 | Gell |
| 2012/0289858 A1 | 11/2012 | Ouyang |
| 2012/0300999 A1 | 11/2012 | Bayer |
| 2013/0053646 A1 | 2/2013 | Yamamoto |
| 2013/0057724 A1 | 3/2013 | Miyahara |
| 2013/0060086 A1 | 3/2013 | Talbert |
| 2013/0066297 A1 | 3/2013 | Shtul |
| 2013/0077257 A1 | 3/2013 | Tsai |
| 2013/0085329 A1 | 4/2013 | Morrissette |
| 2013/0109916 A1 | 5/2013 | Levy |
| 2013/0116506 A1 | 5/2013 | Bayer |
| 2013/0131447 A1 | 5/2013 | Benning |
| 2013/0137930 A1 | 5/2013 | Menabde |
| 2013/0141557 A1 | 6/2013 | Kawata |
| 2013/0150671 A1 | 6/2013 | Levy |
| 2013/0158344 A1 | 6/2013 | Taniguchi |
| 2013/0169843 A1 | 7/2013 | Ono |
| 2013/0172670 A1 | 7/2013 | Levy |
| 2013/0172676 A1 | 7/2013 | Levy |
| 2013/0197309 A1 | 8/2013 | Sakata |
| 2013/0197556 A1 | 8/2013 | Shelton |
| 2013/0222640 A1 | 8/2013 | Baek |
| 2013/0253268 A1 | 9/2013 | Okada |
| 2013/0264465 A1 | 10/2013 | Dai |
| 2013/0267778 A1 | 10/2013 | Rehe |
| 2013/0271588 A1 | 10/2013 | Kirma |
| 2013/0274551 A1 | 10/2013 | Kirma |
| 2013/0281925 A1 | 10/2013 | Benscoter |
| 2013/0296649 A1 | 11/2013 | Kirma |
| 2013/0303979 A1 | 11/2013 | Stieglitz |
| 2013/0317295 A1 | 11/2013 | Morse |
| 2014/0018624 A1 | 1/2014 | Bayer |
| 2014/0031627 A1 | 1/2014 | Jacobs |
| 2014/0046136 A1 | 2/2014 | Bayer |
| 2014/0107418 A1 | 4/2014 | Ratnakar |
| 2014/0148644 A1 | 5/2014 | Levi |
| 2014/0184766 A1 | 7/2014 | Amling |
| 2014/0213850 A1 | 7/2014 | Levy |
| 2014/0225998 A1 | 8/2014 | Dai |
| 2014/0276207 A1 | 9/2014 | Ouyang |
| 2014/0296628 A1 | 10/2014 | Kirma |
| 2014/0296643 A1 | 10/2014 | Levy |
| 2014/0296866 A1 | 10/2014 | Salman |
| 2014/0298932 A1 | 10/2014 | Okamoto |
| 2014/0309495 A1 | 10/2014 | Kirma |
| 2014/0316198 A1 | 10/2014 | Krivopisk |
| 2014/0316204 A1 | 10/2014 | Ofir |
| 2014/0320617 A1 | 10/2014 | Parks |
| 2014/0333742 A1 | 11/2014 | Salman |
| 2014/0333743 A1 | 11/2014 | Gilreath |
| 2014/0336459 A1 | 11/2014 | Bayer |
| 2014/0343358 A1 | 11/2014 | Hameed |
| 2014/0343361 A1 | 11/2014 | Salman |
| 2014/0343489 A1 | 11/2014 | Lang |
| 2014/0364691 A1* | 12/2014 | Krivopisk .......... A61B 1/00096 600/109 |
| 2014/0364692 A1 | 12/2014 | Salman |
| 2014/0364694 A1 | 12/2014 | Avron |
| 2015/0005581 A1 | 1/2015 | Salman |
| 2015/0045614 A1 | 2/2015 | Krivopisk |
| 2015/0057500 A1 | 2/2015 | Salman |
| 2015/0094536 A1 | 4/2015 | Wieth |
| 2015/0099925 A1 | 4/2015 | Davidson |
| 2015/0099926 A1 | 4/2015 | Davidson |
| 2015/0105618 A1 | 4/2015 | Levy |
| 2015/0164308 A1 | 6/2015 | Ratnakar |
| 2015/0182105 A1 | 7/2015 | Salman |
| 2015/0196190 A1 | 7/2015 | Levy |
| 2015/0201827 A1 | 7/2015 | Sidar |
| 2015/0208900 A1 | 7/2015 | Vidas |
| 2015/0208909 A1 | 7/2015 | Davidson |
| 2015/0223676 A1 | 8/2015 | Bayer |
| 2015/0230698 A1 | 8/2015 | Cline |
| 2015/0305601 A1 | 10/2015 | Levi |
| 2015/0313445 A1 | 11/2015 | Davidson |
| 2015/0313450 A1 | 11/2015 | Wieth |
| 2015/0313451 A1 | 11/2015 | Salman |
| 2015/0320300 A1 | 11/2015 | Gershov |
| 2015/0342446 A1 | 12/2015 | Levy |
| 2015/0359415 A1 | 12/2015 | Lang |
| 2015/0374206 A1 | 12/2015 | Shimony |
| 2016/0015257 A1 | 1/2016 | Levy |
| 2016/0015258 A1 | 1/2016 | Levin |
| 2016/0058268 A1 | 3/2016 | Salman |

FOREIGN PATENT DOCUMENTS

| | | |
|---|---|---|
| CA | 2812097 | 3/2012 |
| CA | 2798716 | 6/2013 |
| CA | 2798729 | 6/2013 |
| CN | 103348470 | 10/2013 |
| CN | 103403605 | 11/2013 |
| CN | 103491854 | 1/2014 |
| CN | 103702604 | 4/2014 |
| CN | 103732120 | 4/2014 |
| CN | 104717916 | 6/2015 |
| CN | 105246393 | 1/2016 |
| CN | 105324065 | 2/2016 |
| CN | 105324066 | 2/2016 |
| CN | 105338875 | 2/2016 |
| CN | 105358042 | 2/2016 |
| CN | 105358043 | 2/2016 |
| CN | 105377106 | 3/2016 |
| CN | 105407788 | 3/2016 |
| DE | 202010016900 | 5/2011 |
| EP | 1690497 | 8/2006 |
| EP | 1835844 | 9/2007 |
| EP | 1968425 | 9/2008 |
| EP | 1986541 | 11/2008 |
| EP | 1988813 | 11/2008 |
| EP | 2023794 | 2/2009 |
| EP | 2023795 | 2/2009 |
| EP | 2190341 | 6/2010 |
| EP | 2211683 | 8/2010 |
| EP | 2457492 | 5/2012 |
| EP | 2457493 | 5/2012 |
| EP | 1988812 | 11/2012 |
| EP | 2520218 | 11/2012 |
| EP | 2604175 | 6/2013 |
| EP | 2618718 | 7/2013 |

(56) References Cited

FOREIGN PATENT DOCUMENTS

| | | |
|---|---|---|
| EP | 2635932 | 9/2013 |
| EP | 2648602 | 10/2013 |
| EP | 2649648 | 10/2013 |
| EP | 2672878 | 12/2013 |
| EP | 2736400 | 6/2014 |
| EP | 2744390 | 6/2014 |
| EP | 2442706 | 11/2014 |
| EP | 2865322 | 4/2015 |
| EP | 2908714 | 8/2015 |
| EP | 2979123 | 2/2016 |
| EP | 2991537 | 3/2016 |
| EP | 2994032 | 3/2016 |
| EP | 2994033 | 3/2016 |
| EP | 2994034 | 3/2016 |
| EP | 2996536 | 3/2016 |
| EP | 2996541 | 3/2016 |
| EP | 2996542 | 3/2016 |
| EP | 2996621 | 3/2016 |
| GB | 12196628 | 3/2015 |
| JP | H1043129 | 2/1998 |
| JP | H10239740 | 9/1998 |
| JP | 11137512 | 5/1999 |
| JP | 2005253543 | 9/2005 |
| JP | 2006025888 | 2/2006 |
| JP | 2006068109 | 3/2006 |
| JP | 2010178766 A | 8/2010 |
| JP | 2012135432 | 7/2012 |
| JP | 2013116277 A2 | 6/2013 |
| JP | 2013123647 | 6/2013 |
| JP | 2013123648 | 6/2013 |
| JP | 2013208459 | 10/2013 |
| JP | 2013215582 | 10/2013 |
| JP | 2013230383 | 11/2013 |
| JP | 2013542467 | 11/2013 |
| JP | 2013544617 | 12/2013 |
| JP | 2014524303 | 9/2014 |
| JP | 2014524819 | 9/2014 |
| JP | 2015533300 | 11/2015 |
| WO | 2006073676 | 7/2006 |
| WO | 2006073725 | 7/2006 |
| WO | 2007070644 | 6/2007 |
| WO | 2007092533 | 8/2007 |
| WO | 2007092636 | 8/2007 |
| WO | 2007087421 | 11/2007 |
| WO | 2007136859 | 11/2007 |
| WO | 2007136879 | 11/2007 |
| WO | 2008015164 | 2/2008 |
| WO | 2009014895 | 1/2009 |
| WO | 2009015396 | 1/2009 |
| WO | 2009049322 | 4/2009 |
| WO | 2009049324 | 4/2009 |
| WO | 2009062179 | 5/2009 |
| WO | 2010146587 A1 | 12/2010 |
| WO | 2012038958 | 3/2012 |
| WO | 2012056453 A2 | 5/2012 |
| WO | 2012075153 A2 | 6/2012 |
| WO | 2012077116 | 6/2012 |
| WO | 2012077117 A1 | 6/2012 |
| WO | 2012096102 | 7/2012 |
| WO | 2012120507 A1 | 9/2012 |
| WO | 2013014673 | 1/2013 |
| WO | 2013024476 | 2/2013 |
| WO | 2014061023 | 4/2014 |
| WO | 2014160983 | 10/2014 |
| WO | 2014179236 | 11/2014 |
| WO | 2014182723 | 11/2014 |
| WO | 2014182728 | 11/2014 |
| WO | 2014183012 | 11/2014 |
| WO | 2014186230 | 11/2014 |
| WO | 2014186519 | 11/2014 |
| WO | 2014186521 | 11/2014 |
| WO | 2014186525 | 11/2014 |
| WO | 2014186775 | 11/2014 |
| WO | 2014210516 | 12/2014 |
| WO | 2015002847 | 1/2015 |
| WO | 2015047631 | 4/2015 |
| WO | 2015050829 | 4/2015 |
| WO | 2015084442 | 6/2015 |
| WO | 2015095481 | 6/2015 |
| WO | 2015112747 | 7/2015 |
| WO | 2015112899 | 7/2015 |
| WO | 2015134060 | 9/2015 |
| WO | 2015168066 | 11/2015 |
| WO | 2015168664 | 11/2015 |
| WO | 2015171732 | 11/2015 |
| WO | 2015175246 | 11/2015 |
| WO | 2016014581 | 1/2016 |
| WO | 2016033403 | 3/2016 |

OTHER PUBLICATIONS

International Search Report for PCT/US14/38094, dated Nov. 6, 2014.
International Search Report for PCT/US2014/037526, dated Oct. 16, 2014.
International Search Report for PCT/US2014/071085, dated Mar. 27, 2015.
International Search Report for PCT/US2014/58143, dated Jan. 21, 2015.
International Search Report for PCT/US2015/012506, dated Dec. 11, 2015.
International Search Report for PCT/US2015/012751, dated Jun. 26, 2015.
International Search Report for PCT/US2015/027902, dated Jul. 23, 2015.
International Search Report for PCT/US2015/28962, dated Jul. 28, 2015.
International Search Report for PCT/US2015/29421, dated Aug. 7, 2015.
International Search Report for PCT/US2015/41396, dated Sep. 29, 2015.
International Search Report for PCT/US2015/47334, dated Dec. 28, 2015.
International Search Report for PCT/US2015/6548, dated Feb. 26, 2016.
International Search Report for PCT/US2015/66486, dated Dec. 17, 2015.
Office Action dated Feb. 26, 2016 for U.S. Appl. No. 14/274,323.
Office Action dated Feb. 4, 2016, for U.S. Appl. No. 14/271,234.
Corrected Notice of Allowance dated Apr. 13, 2016 for U.S. Appl. No. 13/680,646.
Notice of Allowance dated Mar. 28, 2016 for U.S. Appl. No. 13/413,059.
Notice of Allowance dated Mar. 29, 2016 for U.S. Appl. No. 13/680,646.
Office Action dated Mar. 23, 2016 for U.S. Appl. No. 13/713,449.
Office Action dated Mar. 24, 2016 for U.S. Appl. No. 13/212,627.
Office Action dated Mar. 28, 2016 for U.S. Appl. No. 13/119,032.
Office Action dated May 25, 2016 for U.S. Appl. No. 14/271,234.
Office Action dated May 5, 2016 for U.S. Appl. No. 14/278,338.
Office Action dated May 6, 2016 for U.S. Appl. No. 14/263,896.
Office Action dated Dec. 27, 2016 for U.S. Appl. No. 14/603,137.
Notice of Allowance dated Apr. 12, 2017 for U.S. Appl. No. 14/603,137.
Office Action dated Jun. 30, 2016 for U.S. Appl. No. 13/655,120.
Office Action dated Jun. 28, 2016 for U.S. Appl. No. 14/278,293.
Office Action dated Jul. 1, 2016 for U.S. Appl. No. 14/229,699.
Office Action dated Jul. 15, 2016 for U.S. Appl. No. 14/273,923.
Notice of Allowance dated Jul. 15, 2016 for U.S. Appl. No. 14/274,323.
Office Action dated Jul. 22, 2016 for U.S. Appl. No. 14/549,265.
Sherman L.M., Plastics That Conduct Hear, Plastics Technology, Jun. 2001—article obtained online from http://www.otonline.com/articles/plastics-that-conduct-heat.
Office Action dated Aug. 11, 2016 for U.S. Appl. No. 14/318,249.
Office Action dated Apr. 28, 2016 for U.S. Appl. No. 13/992,014.
Notice of Allowance dated Aug. 26, 2016 for U.S. Appl. No. 13/212,627.

(56) References Cited

OTHER PUBLICATIONS

Office Action dated Sep. 2, 2016 for U.S. Appl. No. 14/278,338.
Office Action dated Sep. 16, 2016 for U.S. Appl. No. 13/992,014.
Notice of Allowance dated Oct. 12, 2016 for U.S. Appl. No. 13/119,032.
Office Action dated Oct. 7, 2016 for U.S. Appl. No. 13/713,449.
Office Action dated Oct. 5, 2016 for U.S. Appl. No. 14/271,270.
Notice of Allowance dated Oct. 13, 2016 for U.S. Appl. No. 14/273,923.
Notice of Allowance dated Nov. 9, 2016 for U.S. Appl. No. 13/557,114.
Office Action dated Dec. 1, 2016 for U.S. Appl. No. 14/278,293.
Office Action dated Dec. 9, 2016 for U.S Appl. No. 14/549,265.
Office Action dated Dec. 16, 2016 for U.S. Appl. No. 14/263,896.
Notice of Allowance dated Dec. 28, 2016 for U.S. Appl. No. 14/229,699.
Notice of Allowance dated Dec. 27, 2016 for U.S. Appl. No. 14/317,863.
Office Action dated Dec. 29, 2016 for U.S. Appl. No. 15/077,513.
Office Action dated Dec. 30, 2016 for U.S. Appl. No. 14/457,268.
Office Action dated Jan. 17, 2017 for U.S. Appl. No. 14/318,189
Notice of Allowance dated Jan. 31, 2017 for U.S. Appl. No. 14/271,234.
Office Action dated Feb. 2, 2017 for U.S. Appl. No. 14/278,338
Office Action dated Feb. 9, 2017 for U.S. Appl. No. 14/746,986.
Office Action dated Feb. 6, 2017 for U.S. Appl. No. 14/751,835.
Office Action dated Feb. 14, 2017 for U.S. Appl. No. 14/271,270.
Office Action dated Feb. 23, 2017 for U.S. Appl. No. 14/318,249.
Office Action dated Mar. 9, 2017 for U.S. Appl. No. 14/791,316.
Office Action dated Mar. 21, 2017 for U.S. Appl. No. 13/992,014.
Office Action dated Mar. 20, 2017 for U.S. Appl. No. 14/278,293.
Notice of Allowance dated Mar. 21, 2017 for U.S. Appl. No. 14/549,265.
Office Action dated Mar. 22, 2017 for U.S. Appl. No. 14/705,355.
Office Action dated Mar. 24, 2017 for U.S. Appl. No. 14/838,509.
Notice of Allowance dated Apr. 18, 2017 for U.S. Appl. No. 13/713,449.
Office Action dated Apr. 19, 2017 for U.S. Appl. No. 14/988,551.
Notice of Allowability dated Apr. 21, 2017 for U.S. Appl. No. 14/549,265.
Office Action dated May 11, 2017 for U.S. Appl. No. 14/278,293.
Office Action dated May 10, 2017 for U.S. Appl. No. 14/988,551.
Office Action dated May 5, 2017 for U.S. Appl. No. 15/077,513.
Notice of Allowance dated May 15, 2017 for U.S. Appl. No. 14/271,270.
Office Action dated May 15, 2017 for U.S. Appl. No. 14/278,293.
Office Action dated May 18, 2017 for U.S. Appl. No. 14/278,338.
Notice of Allowance dated May 16, 2017 for U.S. Appl. No. 14/746,986.
Office Action dated May 23, 2017 for U.S. Appl. No. 13/655,120.
Notice of Allowance dated May 25, 2017 for U.S. Appl. No. 14/318,189.
Office Action dated May 23, 2017 for U.S. Appl. No. 14/500,975.

\* cited by examiner

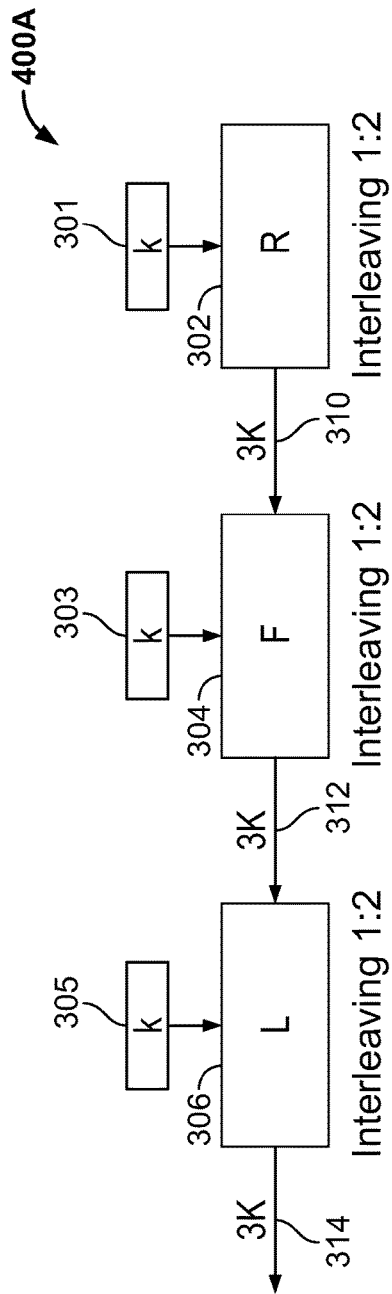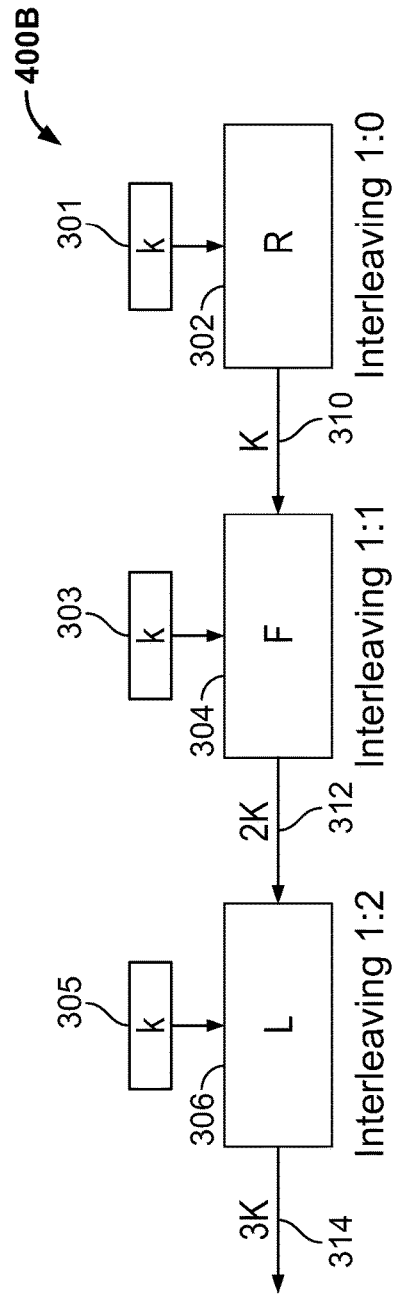

IMAGE CAPTURE AND VIDEO PROCESSING SYSTEMS AND METHODS FOR MULTIPLE VIEWING ELEMENT ENDOSCOPES

CROSS-REFERENCE TO RELATED APPLICATIONS

The present application is a division application of U.S. patent application Ser. No. 14/603,137, entitled "Image Capture and Video Processing Systems and Methods for Multiple Viewing Element Endoscopes" and filed on Jan. 22, 2015, which relies on, for priority, the following United States Provisional Patent Applications, which are herein incorporated by reference in their entirety:

U.S. Provisional Patent Application No. 61/930,101, entitled "Daisy Chain Multi-Sensor Endoscopic System" and filed on Jan. 22, 2014;

U.S. Provisional Patent Application No. 61/948,012, entitled "Parallel Illuminating Systems" and filed on Mar. 4, 2014.

The present application relates to U.S. patent application Ser. No. 13/655,120, entitled "Multi-Viewing Element Endoscope", and filed on Oct. 18, 2012.

In addition, the present application also relates to U.S. patent application Ser. No. 13/882,004, entitled "Optical System for Multi-Sensor Endoscopes", filed on Apr. 26, 2013, which is a 371 National Stage Entry of PCT Application Number PCT/IL11/000832, of the same title, and filed on Oct. 27, 2011, which, in turn, relies upon U.S. Provisional Patent Application No. 61/407,495, filed on Oct. 28, 2010.

The present application also relates to U.S. patent application Ser. No. 13/992,014, entitled "Flexible Electronic Circuit Board for a Multi-Camera Endoscope", filed on Jun. 6, 2013, which is a 371 National Stage Entry of PCT Application Number PCT/IL11/050049, of the same title, and filed on Dec. 8, 2011, which, in turn, relies upon U.S. Provisional Patent Application No. 61/421,238, filed on Dec. 9, 2010.

All of the above-mentioned applications are herein incorporated by reference in their entirety.

FIELD

The invention relates generally to endoscopy systems and, in particular, to image capture and video processing systems and methods in multiple-viewing element and multiple-sensor endoscope systems.

BACKGROUND

Free space is an extremely valuable resource within a multiple camera endoscope tip section. Such tip sections typically include a plurality of cameras, a plurality of optical systems, a plurality of illuminators, a flexible electronic circuit board configured to support and encapsulate the components and a working channel configured for the injection of fluids and for the insertion of miniscule surgery tools.

An optical system for a tip section of a multiple sensor endoscope comprising a front-pointing camera sensor, a front objective lens system, a side-pointing camera-sensor, and a side objective lens system is disclosed in U.S. patent application Ser. No. 13/882,004, entitled "Optical Systems for Multi-Sensor Endoscopes" and filed on May 23, 2013, which is herein incorporated by reference in its entirety.

A flexible electronic circuit board for a multiple camera endoscope tip section is disclosed in Patent Cooperation Treaty Application Number PCT/IL2011/050049, entitled "Flexible Electronic Circuit Board for a Multi-Camera Endoscope" and filed on Dec. 8, 2011, which is herein incorporated by reference in its entirety. The circuit board comprises: a front camera surface configured to carry a forward looking camera; a first side camera surface configured to carry a first side looking camera; a second side camera surface configured to carry a second side looking camera; one or more front illuminator surfaces configured to carry one or more front illuminators; and, one or more side illuminators surfaces configured to carry one or more side illuminators.

The flexible circuit board is connected to the central control unit via a multi-wire cable. The multi-wire cable is welded on the board in a designated location, freeing additional space within the tip section assembly and adding flexibility to the cable access.

A multiple sensor or multiple viewing elements endoscope tip section comprising a front-pointing camera and two or more side-pointing cameras positioned at or in proximity to a distal end of the tip section and a working channel configured for insertion of a surgical tool is disclosed in U.S. patent application Ser. No. 13/655,120, entitled "Multi-Camera Endoscope" and filed on Oct. 18, 2012, which is herein incorporated by reference in its entirety, and assigned to the Applicant of the present specification. As described in the '120 application, the field of view (FOV) of each camera sensor in a multiple sensor endoscope is illuminated by two or more illuminators that are light emitting diodes (LEDs). Thus, multiple sensor endoscopes' tips that include a right pointing camera or viewing element, a front pointing camera or viewing element and a left pointing camera or viewing element may include a minimum of 9 or more LEDs. Since the FOVs' depth in different orientations, for example in a patient's colon, can vary significantly during a colonoscopy procedure, illuminating all LEDs with a fixed illumination intensity is sub-optimal, may be too weak in some orientations for example and may drive the camera sensor arrays beyond their dazzle limits due to light reflection from a nearby wall in other orientations.

One approach for controlling the illumination of a multiple illuminator endoscope system may be provided by dynamically controlling the emitted light intensities. However, since multiple illuminator endoscope systems may include 10 or more illuminators, controlling the light intensity of each illuminator independent of the other illuminators dynamically may be a difficult task.

Multiple-camera/viewing element endoscope digital image processing is a computationally demanding task. Typically, each image sensor within each viewing element captures 50 to 60 frames per second (progressive scanning) or 50 to 60 fields per second (interlaced scanning). Each frame includes, within a high definition (HD) video mode, 1920×1080 pixels, summing up to more than 2 million pixels per frame where each RGB (red, green, blue) pixel is encoded by 3 data bytes. A multiple camera endoscope comprising a front pointing camera and two side pointing cameras typically generates about 75,000 video packets per frame, with a 60 frames per second rate, which sums up to approximately 1 Gigabyte (GB) per second.

Signal processors that can manage such high data rates are too large to be placed within a multiple camera endoscope tip section. Thus, multiple camera endoscopes need to process and transfer the video packet data stream of approximately 1 GB/second through the endoscope body via wires connected to an external display.

Since free space is such a valuable resource, the number of control and power lines used for data transfer from the endoscope tip section and for the endoscope tip's illuminating system, through the endoscope elongated body, and to a central control unit, should be minimized.

Therefore, it would be highly advantageous to provide "daisy-chained" multiple camera endoscope systems configured to transmit video data over a single serial line, which can optimize overall system performance.

While daisy-chained, serially connected illuminators of multiple camera endoscope systems can provide optimized overall system performance in one system configuration, some drawbacks may include:

1. Identical current flow through serially connected LEDs that is dictated by the current flow of the LED that illuminates with the most power at a particular moment. Thus, power may be wasted, which may heat the endoscope's tip section, and furthermore, may over-expose the sensors' arrays in excessively illuminated regions.
2. The supply voltage in a daisy chain of serially connected LEDs is proportional to the number of chained LEDs. Therefore, the number of LEDs that may be chained in endoscope's tip section is limited for at least safety reasons. Having a multiple number of control and power lines for each LED connected in parallel to a controller may solve these concerns, but it may waste a valuable volume at the endoscope's tip section.

As such, it would also be highly advantageous to provide parallel illuminating systems that require a minimal number of control and power lines and allow for regulation of each illuminator's illumination intensity independently.

SUMMARY

In some embodiments, the present specification discloses a daisy chain multiple sensor system comprising a plurality of daisy chained image sensors, wherein at least one of said daisy chained image sensors comprises: a sensor array to capture images and generate video packets from said captured images; a compression unit to compress said video packets and generate compressed video packets; a self-packet buffer configured to store said compressed video packets; a de-serializer unit configured to receive serialized video packets from a previous-in-chain image sensor and convert said serialized video packets to parallel video packets; a chained packet buffer configured to store said parallel video packets corresponding to the previous-in-chain image sensor; an arbitration unit configured to interleave the video packets stored in the self-packet buffer and the chained packet buffer; a serial unit to serially output the interleaved video packets; and, a central control circuit configured to manage said compression unit, self-packet buffer, de-serializer unit, chained packet buffer, arbitration unit and serial unit.

Optionally, the daisy chain multiple sensor system is an endoscopic system.

In some embodiments, the at least one of said plurality of daisy chained image sensors may be arranged as a system-on-chip ASIC.

Optionally, the compression unit, self-packet buffer, chained packet buffer, arbitration unit, serial unit and central control circuit are arranged as a system-on-chip ASIC, and wherein said sensor array is external to said ASIC.

Optionally, said central control circuit is configured to de-interleave the interleaved video packets and re-generate separated images as captured by said plurality of daisy chain image sensors.

Optionally, only a last-in-chain serial unit is connected to an input of said central control circuit by a single serial line.

In some embodiments, said plurality of daisy chained image sensors may comprise a first daisy chained image sensor, a second daisy chained image sensor and a third daisy chained image sensor. Optionally, said first daisy chained image sensor is a first side-pointing image sensor, said second daisy chained image sensor is a front pointing image sensor and said third daisy chained image sensor is a second side-pointing image sensor of an endoscope tip.

In some embodiments, at least one of said plurality of daisy chained image sensors may comprise an identifier.

Optionally, said compression unit is configured to add packet headers to said video packets. Optionally, said packet headers comprise image sensor identifiers. Optionally, said packet headers further comprise time stamps and/or coordinate identifiers.

Optionally, said compression unit is configured to generate video packets comprising 256 bytes to 4 Kbytes per packet.

Optionally, self-packet buffer and chained packet buffer size is 2 to 64 Kbytes.

Optionally, self and chained packet buffers are configured to store data at 0.1 Gigabits to 10 Gigabits per second rate.

Optionally, said arbitration unit is configured to draw and interleave, alternately, one video packet from said self-packet buffer and two video packets from said chained packet buffer. Still optionally, said arbitration unit is configured to draw and interleave, alternately, one video packet from said self-packet buffer and a variable number of video packets from said chained packet buffer.

Optionally, serial units of said plurality of daisy chained image sensors are configured to transfer serial data at identical bitrate.

Optionally, the serial unit is configured to transfer serial data at bitrates that depends on a position of the image sensor in the daisy chained multiple sensor system, and wherein the serial unit data transfer rate of the image sensor is n+1 times the serial unit data transfer rate of a previous-in-chain image sensor, where n is a number of preceding image sensors in said daisy chained multiple sensor system.

Optionally, said serial unit is configured to transfer data at a rate of 0.1 Gigabits to 10 Gigabits per second.

Optionally, said plurality of daisy chained image sensors are configured to capture frames with identical frame rate. Still optionally, said plurality of daisy chained image sensors are configured to capture frames with a variable frame rate that depends on the image sensor position in said daisy chain.

Optionally, in some embodiments, the frame rates may vary dynamically.

In some embodiments, commands to configure a mode of operation of at least one of said daisy chained image sensors as well as status related to the mode of operation is communicated back to the central control circuit as ancillary data packets interleaved with the video packets.

In some embodiments, said central control circuit may be positioned at a proximal end of an endoscope. In other embodiments, said central control circuit may be located in a device external to an endoscope.

In some embodiments, said plurality of daisy chained image sensors may be charge coupled device (CCD) sensors or complementary metal oxide semiconductor (CMOS) sensors.

In some embodiments, the present specification discloses a video processing method for use in an endoscopy system, said endoscopy system having a plurality of daisy chained image sensors and a central control unit in data communication with said plurality of daisy chained image sensors, the method comprising: in a first of the plurality of daisy chained image sensors, generating video packets from images captured by a sensor array of the first of the plurality of daisy chained image sensors and storing said video packets in a self-packet buffer; and in said first of the plurality of daisy chained image sensors, interleaving video packets of said self-packet buffer and at least one void packet of a chained packet buffer and transmitting the interleaved video packets to another of the plurality of daisy chained image sensors.

Optionally, the central control unit outputs generates three separate and distinct video images from the interleaved video packets and transmits the three separate and distinct video images to three separate displays.

Optionally, the step of generating video packets from images further comprises compressing said video packets.

Optionally, said transmitting of the interleaved packets is performed with identical gross bitrate that does not depend on a position of the image sensors in said plurality of daisy chained image sensors.

Optionally, said transmitting of the interleaved packets is performed with variable bitrates that depends on a position of the image sensors in said plurality of daisy chained image sensors, and wherein a data transfer rate of an image sensor is n+1 times the data transfer rate of a previous-in-chain image sensor, where n is the number of preceding image sensors in said plurality of daisy chained image sensors.

Optionally, an image capture frame rate of said plurality of daisy chained image sensors depends on a position of the image sensors in said plurality of daisy chained image sensors.

Still optionally, an image capture frame rate of said plurality of daisy chained image sensors varies dynamically.

In some embodiments, the present specification discloses a video processing method for use in an endoscopy system, said endoscopy system having a plurality of daisy chained image sensors and a central control unit in data communication with said plurality of daisy chained image sensors, the method comprising: in a second of the plurality of daisy chained image sensors, generating video packets from images captured by a sensor array of the second of the plurality of daisy chained image sensors and storing said video packets in a self-packet buffer; in said second of the plurality of daisy chained image sensors, storing in a chain packet buffer video packets received from another of the plurality of daisy chained image sensors; and in said second of the plurality of daisy chained image sensors, interleaving video packets of said self-packet buffer and said chained packet buffer and transmitting the interleaved video packets to another of the plurality of daisy chained image sensors.

Optionally, the central control unit outputs generates three separate and distinct video images from the interleaved video packets and transmits the three separate and distinct video images to three separate displays.

Optionally, the step of generating video packets from images further comprises compressing said video packets.

Optionally, said transmitting of the interleaved packets is performed with identical gross bitrate that does not depend on a position of the image sensors in said plurality of daisy chained image sensors.

Optionally, said transmitting of the interleaved packets is performed with variable bitrates that depends on a position of the image sensors in said plurality of daisy chained image sensors, and wherein a data transfer rate of an image sensor is n+1 times the data transfer rate of a previous-in-chain image sensor, where n is the number of preceding image sensors in said plurality of daisy chained image sensors.

Optionally, an image capture frame rate of said plurality of daisy chained image sensors depends on a position of the image sensors in said plurality of daisy chained image sensors.

Still optionally, an image capture frame rate of said plurality of daisy chained image sensors varies dynamically.

In some embodiments, the present specification discloses a video processing method for use in an endoscopy system, said endoscopy system having a plurality of daisy chained image sensors and a central control unit in data communication with said plurality of daisy chained image sensors, the method comprising: in a second of the plurality of daisy chained image sensors, generating video packets from images captured by a sensor array of the second of the plurality of daisy chained image sensors and storing said video packets in a self-packet buffer; and in said second of the plurality of daisy chained image sensors, interleaving video packets of said self-packet buffer and at least one void packet of a chained packet buffer and transmitting the interleaved video packets to another of the plurality of daisy chained image sensors.

Optionally, the central control unit outputs generates three separate and distinct video images from the interleaved video packets and transmits the three separate and distinct video images to three separate displays.

Optionally, the step of generating video packets from images further comprises compressing said video packets.

Optionally, said transmitting of the interleaved packets is performed with identical gross bitrate that does not depend on a position of the image sensors in said plurality of daisy chained image sensors.

Optionally, said transmitting of the interleaved packets is performed with variable bitrates that depends on a position of the image sensors in said plurality of daisy chained image sensors, and wherein a data transfer rate of an image sensor is n+1 times the data transfer rate of a previous-in-chain image sensor, where n is the number of preceding image sensors in said plurality of daisy chained image sensors.

Optionally, an image capture frame rate of said plurality of daisy chained image sensors depends on a position of the image sensors in said plurality of daisy chained image sensors.

Still optionally, an image capture frame rate of said plurality of daisy chained image sensors varies dynamically.

In some embodiments, the present specification discloses a video processing method for use in an endoscopy system, said endoscopy system having a plurality of daisy chained image sensors and a central control unit in data communication with said plurality of daisy chained image sensors, the method comprising: in a third of the plurality of daisy chained image sensors, generating video packets from images captured by a sensor array of the third of the plurality of daisy chained image sensors and storing said video packets in a self-packet buffer; in said third of the plurality of daisy chained image sensors, storing in a chain packet buffer video packets received from another of the plurality of daisy chained image sensors; in said third of the plurality of daisy chained image sensors, interleaving video packets of said self-packet buffer and said chained packet buffer and transmitting the interleaved video packets to a central control unit; and in said central control unit, de-interleaving said interleaved video packets and outputting de-interleaved and separated image frames captured by said plurality of daisy chained image sensors.

Optionally, the central control unit outputs or generates three separate and distinct video images from the interleaved video packets and transmits the three separate and distinct video images to three separate displays.

Optionally, the step of generating video packets from images further comprises compressing said video packets.

Optionally, said transmitting of the interleaved packets is performed with identical gross bitrate that does not depend on a position of the image sensors in said plurality of daisy chained image sensors.

Optionally, said transmitting of the interleaved packets is performed with variable bitrates that depends on a position of the image sensors in said plurality of daisy chained image sensors, and wherein a data transfer rate of an image sensor is n+1 times the data transfer rate of a previous-in-chain image sensor, where n is the number of preceding image sensors in said plurality of daisy chained image sensors.

Optionally, an image capture frame rate of said plurality of daisy chained image sensors depends on a position of the image sensors in said plurality of daisy chained image sensors.

Still optionally, an image capture frame rate of said plurality of daisy chained image sensors varies dynamically.

In accordance with other embodiments, the present specification describes parallel illuminating systems that allow regulation of each illuminator's illumination intensity independently.

In some embodiments, regulating each illuminator's illumination intensity may allow for illumination of different orientations with different illumination intensities.

In some embodiments, regulating each illuminator's illumination intensity may reduce the overall power consumption of the endoscope and thus may reduce heat production in the endoscope's tip section.

Optionally, regulating each illuminator's illumination intensity independently may allow for different types of illuminators may be switched on or switched off on demand.

In other embodiments, the present specification discloses a parallel illuminating system, the system comprising: at least one camera sensor configured to capture images; at least two illuminators connected in parallel to a power supply line and configured to illuminate a plurality of field of views (FOVs) associated with said at least one camera sensor, wherein said at least two illuminators are associated with at least one illuminator circuit; a central control circuit to communicate control signals over the power supply line, said control signals being superimposed over input power to said at least one illuminator circuit; and, a logic circuit within said at least one illuminator circuit to receive said control signals superimposed over the input power, wherein said logic circuit comprises a power extraction module to extract the input power and a data extraction module to decode said control signals in order to determine a desired current flow through said at least two illuminators.

Optionally, said logic circuit and said central control circuit include processors.

Optionally, said control signals regulate the illumination intensity of each of said at least two illuminators independently. Still optionally, said control signals comprise switching on and off each of said at least two illuminators independently.

Optionally, said control signals and power are provided to said at least two illuminators over said power supply line.

Optionally, said control signals and power are provided to each of said at least two illuminators on separate power supply lines.

Optionally, the processor of said central control circuit is configured to encode control signals and transmit said encoded control signals to said at least two illuminators.

Optionally, the processor of said logic circuit is configured to decode said encoded control signals. Optionally, the encoded control signals comprise signals for varying an electric current flow through each of said at least two illuminators. Still optionally, the encoded control signals are communicated over said power supply line using a universal-asynchronous-receiver-transmitter (UART) protocol. Still optionally, the encoded control signals comprise encoded IDs of each of said at least two illuminators and wherein the processors of said logic circuits associated with each of said at least two illuminators are configured to decode said encoded illuminators' IDs and regulate intensities of said at least two illuminators according to said encoded control signals.

Optionally, the processor of said central control circuit is configured to detect high intensity reflections received by said at least one camera sensor and reduce the illumination intensity of at least one of said at least two illuminators.

Still optionally, the processor of said central control circuit is configured to detect low intensity reflections received by said at least one camera sensor and increase the illumination intensity of at least one of said at least two illuminators.

Optionally, the central control circuit is configured to vary the illumination intensity of each of said at least two illuminators manually.

Optionally, said at least two illuminators comprise at least one light emitting diode (LED). Still optionally, the logic circuits associated with said at least two illuminators control current flows through said at least one LED.

Optionally, the processor of said logic circuit is implemented as application specific integrated circuits (ASICs). Still optionally, the processor of said logic circuit is implemented as field programmable gate arrays (FPGAs).

Optionally, each of said at least two illuminators has a light wavelength range which is different compared to the other.

In some embodiments, one or more additional illuminators may be connected in series to one or more of said at least two illuminators connected in parallel to said power supply line.

Optionally, said parallel illuminators system is an illumination system of an endoscope tip.

Optionally, said central control circuit is a camera board (CB) circuit of an endoscope tip.

Optionally, said logic circuit further comprises a temperature sensor. Still optionally, said temperature sensor is configured to sense at least one temperature at a plurality of junctions within illuminator circuits of said at least two illuminators, from which the temperature of a tip section of an endoscope is calculated. Still optionally, the processor of said central control circuit regulates said at least two illuminators' emitted light according to said sensed temperatures.

In some embodiments, said logic circuit may further comprise at least one motion sensor selected from a group consisting of: accelerometers, gyros and combinations thereof.

Optionally, the processor of said central control circuit regulates said at least two illuminators' illumination intensity according to indications of said at least one motion sensor. Still optionally, said at least one motion sensor is a MEMS device.

Optionally, said at least one camera sensor is a CCD array or a CMOS array.

In some embodiments, the present specification discloses a method of controlling illumination of a parallel illuminating system, the method comprising: providing at least one camera sensor configured to capture images, at least two illuminators connected in parallel to a power supply line and configured to illuminate a plurality of FOVs associated with said at least one camera sensor, at least one illuminator circuit associated with said at least two illuminators, and a central control circuit; generating, by said central control circuit, encoded control signals for each one of said at least two illuminators; communicating, over the power supply line, said encoded control signals superimposed over input power to said at least two illuminators; decoding said encoded control signals by a logic circuit associated with said at least one illuminator circuit, wherein said logic circuit comprises a power extraction module to extract the input power and a data extraction module to decode the control signals and producing, by said logic circuit, decoded control signals to determine a desired current flow through said at least two illuminators.

Optionally, said parallel illuminating system is an endoscope tip's illumination system.

Optionally, said generated encoded signals further comprise indications for switching on and switching off each one of said at least two illuminators independently.

Optionally, said generated encoded control signals comprise indications for varying an illumination intensity of each said at least two illuminators independently.

Optionally, said encoded control signals and power to said at least two illuminators are provided on a single power line.

Optionally, said encoded control signals are UART protocol instructions.

Optionally, said encoded control signals to each one of said at least two illuminators comprise a common indication/instruction to said at least two illuminators.

The aforementioned and other embodiments of the present specification shall be described in greater depth in the drawings and detailed description provided below.

BRIEF DESCRIPTION OF THE DRAWINGS

These and other features and advantages of the present specification will be further appreciated, as they become better understood by reference to the detailed description when considered in connection with the accompanying drawings:

FIG. 4A is a flow chart illustrating a fixed rate interleaving data flow, according to certain embodiments of the present specification;

FIG. 4B is a flow chart illustrating a variable rate interleaving data flow, according to certain embodiments of the present specification;

DETAILED DESCRIPTION

Figure 1:
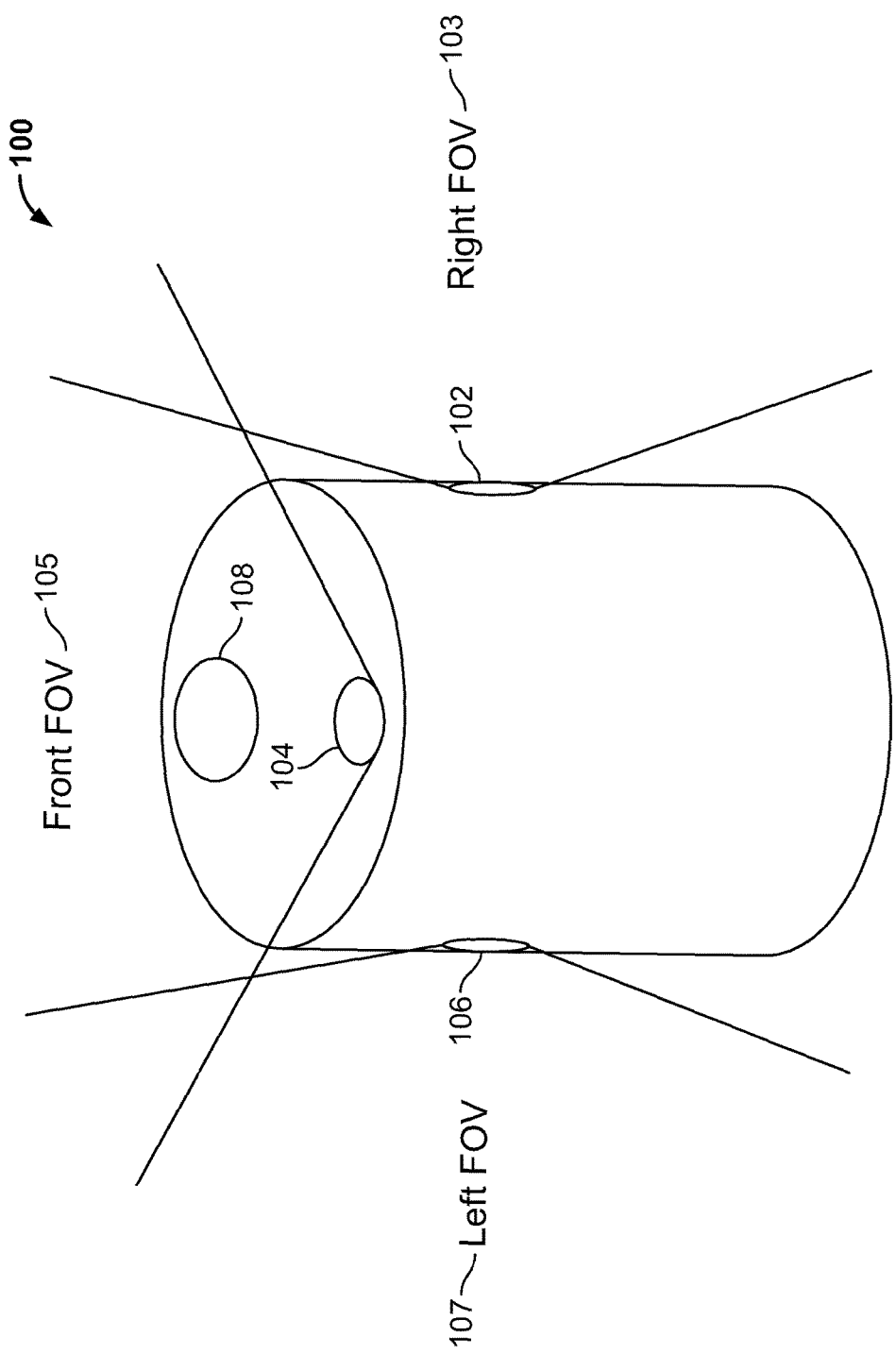
FIG. 1 is a diagram of a multiple sensor endoscope tip section, in which a daisy chain configuration may be employed, according to certain embodiments of the present specification.

In the description and claims of the present specification, each of the words "comprise", "include", and "have", and forms thereof, are not necessarily limited to members in a list with which the words may be associated.

The present specification is directed toward multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present specification is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In accordance with an aspect, the present specification discloses a daisy chain multiple sensor endoscope system and a video processing method. The system includes an endoscope comprising a plurality of daisy chained image sensors and a central control unit. At least one daisy chained image sensor includes a sensor array configured to capture images and generate video packets out of the captured images, a video compression unit configured to optionally compress the video packets, a self-packet buffer configured to store the video packets, a chain packet buffer configured to store video packets received from previous-in-chain image sensors, a serial-to-parallel de-serializer input unit configured to convert serialized input video packets to parallel 8, 16, 32 or 64-bits words, an arbitration unit configured to interleave the stored video packets, a serial output unit configured to output serially the interleaved video packets, and a control circuit configured to manage the video compression unit. The central control unit is configured to de-interleave the video packets and regenerate separated images as captured by the plurality of daisy chain image sensors.

The daisy chain multiple sensor endoscope system is used to display a plurality of images captured by a plurality of image sensors (and thus, viewing elements/cameras) disposed at an endoscope tip section where the image data from the plurality of images is communicated over a single line. As used in conjunction with this embodiment, the term single line refers to coaxial cable, twisted-pair, twinaxial cable (twinax), and the like, either differentially or single-ended.

The daisy chain multiple sensor endoscope system allows further miniaturization of the endoscope tip section and the endoscope body due to communicating the video packet data over a single printed-circuit-board (PCB) serial line (differential, or single-ended). Persons of ordinary skill in the art should appreciate that the aforementioned miniaturization, as a result of daisy-chaining is, with reference to at least the following: a) use of only one soldering point for the serial line instead of multiple soldering points (for example, three) for multiple camera sensors (for example, three camera sensors), b) instead of multiple video trace routings (one for each camera sensor) over longer traces towards the PCB tip, there are shorter routes between adjacent cameras, and a shortened route from a last daisy-chain camera to the PCB tip, c) cabling within an insertion tube of the endoscope is reduced to a single serial line instead of multiple lines corresponding to multiple camera sensors.

The daisy chained multiple sensor endoscope system may, in some cases, require development of a single application specific integrated circuit (ASIC) processor for the plurality of image sensor circuits. Thus, according to some embodiments of the current specification, a single ASIC is designed, fabricated, daisy chained and tested for the daisy chain multiple sensor endoscope system. As used herein, the term "daisy chain(ed) multiple sensor" refers both to a serial chain of sensors (that is, a serial chain of at least two sensors—such as in a gastroscope and at least three sensors—such as in a colonoscope) and to a plurality of serial chains of sensors connected in parallel.

In an embodiment, the serial output units of the plurality of daisy chained image sensor circuits are configured to transfer serial data with an identical gross bitrate. In such a case, this identical gross bitrate should support the sensor that outputs the highest bandwidth of payload data (net bitrate), i.e. the last sensor in the chain. The closer a sensor is located to the beginning of the chain, the more void packets it will transmit to achieve that identical gross bitrate, hence compensating for its lower net bitrate.

In an embodiment, the serial output units of the plurality of daisy chained image sensor circuits are configured to transfer serial data with a bitrate that depends on the position of the image sensor circuit in the chain. The serial output unit data transfer rate of an image sensor circuit may be n+1 times the serial output unit data transfer rate of a previous-in-chain image sensor circuit, where n is the number of preceding image sensor circuits in the image sensor daisy chain. Accordingly, different processing circuits need to be designed for different image sensor circuits in the chain. However, in one embodiment, a single ASIC is designed having multiple processing capabilities that depend on the image sensor circuit position in the chain.

In an embodiment, the image sensor's capturing frame rate depends on the image sensor position in the daisy chain and varies dynamically.

In an embodiment, the image sensor's mode of operation, for example: frame rate, compression strategy, acquired field of view (FOV), output resolution, color space and sampling, are dynamically set by the user.

Reference is now made to FIG. 1, which illustrates an endoscope tip section, in which a daisy chained multiple sensor configuration may be employed, according to certain embodiments of the present specification. The endoscope tip section 100 includes a side pointing image sensor 102 capturing right field of view (FOV) 103, a front pointing image sensor 104 capturing front FOV 105 and a second side pointing image sensor 106 capturing left FOV 107. The endoscope tip section 100 also includes a working channel 108 configured to inject fluids or gases and to insert minuscule surgery tools. Although not seen in FIG. 1, it is understood that the endoscope tip section 100 includes a plurality of illuminators configured to illuminate objects in a patient's colon, for example, a plurality of optical systems that include front and side objective lens systems, and a flexible electronic circuit board configured to carry the front and side camera sensors, illuminators and optical systems.

Figure 2:
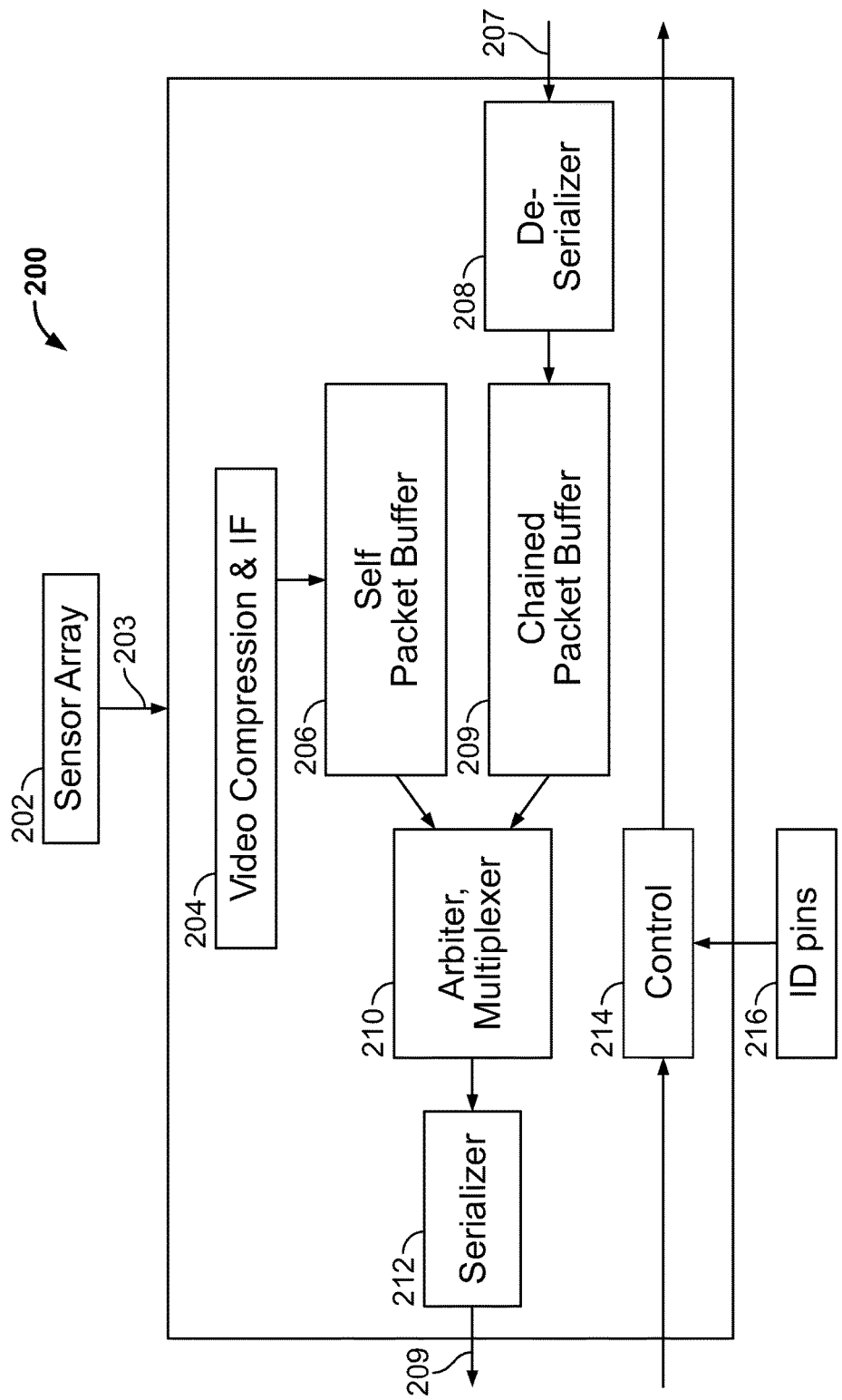
FIG. 2 is an image sensor circuit diagram, according to certain embodiments of the present specification.

Reference is now made to FIG. 2, which illustrates an image sensor circuit according to certain embodiments of the present specification. Image sensor circuit 200 comprises a sensor array 202 that may be a charged couple device (CCD) sensor or a complementary metal oxide semiconductor (CMOS) sensor. According to some embodiments, the terms "image sensor circuit" and "daisy chained image sensor" are interchangeably used. Typically, sensor array 202 is configured to capture 60 frames/images per second of an object and generate video packets, where each high definition (HD) video frame includes 1920×1080 pixels, generating more than 2 million pixels per frame in a progressive HD video mode. Other HD or regular video modes with different number of pixels per frame may be implemented with, and are in the scope of, other embodiments of the current specification—such as, but not limited to, 24, 25, 29.97, 30 frames per second. Moreover, additional exemplary resolutions such as, but not limited to, 600×600, 800×800, 1000×1000, 1200×1200 or more may be used instead of standard HD or SD resolutions.

Image sensor circuit 200 includes a video compression unit 204 connected to array sensor 202. Compression unit 204 generates video packets that include typically, but not limited to, 256 bytes to 4 Kbytes per video packet out of a captured frame. According to HDTV standard, the sensor array pixel clock frequency may be 148.5 MHz and 3 bytes of data may be used to encode each RGB pixel. The generated video packet rate may be 1.74 mega video packets per second and typical data flow from sensor array 202 to compression unit 204 may be 445.5 Megabytes (MB) per second.

In one embodiment, pixel encoding using color space family YCbCr (where Y is luminance, Cb is blue-difference chroma, and Cr is red-difference chroma) with 4:2:2 chroma sampling is used instead of RGB pixel encoding, which reduces encoding to 2 bytes per pixel, thus reducing the encoding by a factor of 0.67 compared to an RGB scheme (YCbCr with 4:2:0 chroma sampling may be used to further reduce the bytes per pixel encoding, in alternate embodiments).

In another embodiment, an interlaced video mode is used, further reducing by half the data flow while vertical resolution reduction is much less than half.

In yet another embodiment, YCbCr 4:2:2 encoding and interlacing video mode is performed, reducing the data flow to about 0.15 Gigabytes per second and less.

In still another embodiment, the array sensors provide video in raw format (that is in its most basic form prior to de-mosaic), hence reducing number of bits per pixels from 16 (YCbCr case) to 10.

Compression unit 204 can compress video packets with 1:2 compression ratio and greater using compression algorithms similar to, for example, zip, jpeg, mpeg and the like.

Image sensor circuit 200 includes self-packet buffer 206 configured to store compressed/encoded video packets generated by compression unit 204. The packet buffer size, for example, can be, but is not limited to, 2 to 64 Kilobytes (KB). According to certain embodiments of the present specification, the self-packet buffer size may be 8 Kilobytes, storing 32 video packets that include 256 bytes per packet. The input sampling rate of the self-packet buffer may be configured to match the video packet data flow rate generated by sensor array 202 and compression unit 204. In the exemplary embodiment described herein, the data flow rate may be 445.5 Mbytes per second or in a range varying from 1 Mbytes to 10 Gbytes per second, however, other frame rates, compression rates, and pixel rates may be generated by sensor array 202 and compression unit 204 and are within the scope of the present specification.

Image sensor circuit 200 includes chained packet buffer 209 configured to store video packets received from previous-in-chain image sensor serial or serializer output 207, after conversion to parallel 8, 16, 32 or 64 bits words by de-serializer 208. The size of the chained packet buffer 209 is similar to the size of the self-packet buffer 206 in accordance with an embodiment. In accordance with an embodiment, the self-packet and chained packet buffers 206, 209 are configured to store data at 0.1 Gigabits to 10 Gigabits per second rate.

Image sensor circuit 200 includes an arbitration and multiplexing unit 210 configured to interleave video packets stored at self-packet buffer 206 and chain packet buffer 209. Two exemplary interleaving schemes are explained in more detail below with reference to FIG. 4A and FIG. 4B.

Image sensor circuit 200 includes a serial output unit or serializer 212 configured to output serially the interleaved video packets received from arbitration unit 210. Serial output unit 212 drives serial data over a single serial line 209 to the next image sensor circuit in chain or to a central control unit disposed at the endoscope proximal end or at an external unit (not shown).

In accordance with an embodiment, the serial output unit 212 is configured to transfer data at 100 Megabits (or less) to 100 Gigabits per second rate. It should be appreciated that 100 Gigabits per second rate is approximately two orders of magnitude than what is achievable on a single copper line.

In one embodiment, the serial output unit 212 is configured to transfer data at 0.1 Gigabits to 10 Gigabits per second rate.

Image sensor circuit 200 includes a control circuit 214 configured to manage/control video compression unit 204, self-packet buffer 206, de-serializer 208, chain packet buffer 209, arbitration unit 210, serial output unit or serializer 212, and the operation mode of sensor array 202. In accordance with some embodiments, the sensor array 202 reports (to the central control unit) its internal operation mode status and receives (from the central control unit) commands for configuring its (202) mode of operation (for example: frame rate, compression strategy, acquired field of view (FOV), output resolution, color space and sampling)—as ancillary data packets interleaved within the video packets. Such embodiments would necessitate a first sensor in the daisy chain to have its serial data input connected to a serial data wire running from a central control unit to the endoscopic tip. The other sensors have their serial data inputs left unconnected to spare PCB space, since they will receive their commands as ancillary command packets, over video lines.

Control circuit 214 is configured to receive ID pins 216, as identifiers, that are used to define a unique identifier of sensor circuit 200.

In some embodiments, image sensor circuit 200 is embedded in a system-on-chip (SOC) ASIC that includes sensor array 202 and control and data processing circuits (214, 204, 206, 208, 209, 210 and 212) on a single chip. Alternatively, image sensor control and data processing circuits may be embedded in an ASIC connected to a separate sensor array 202.

Figure 3A:
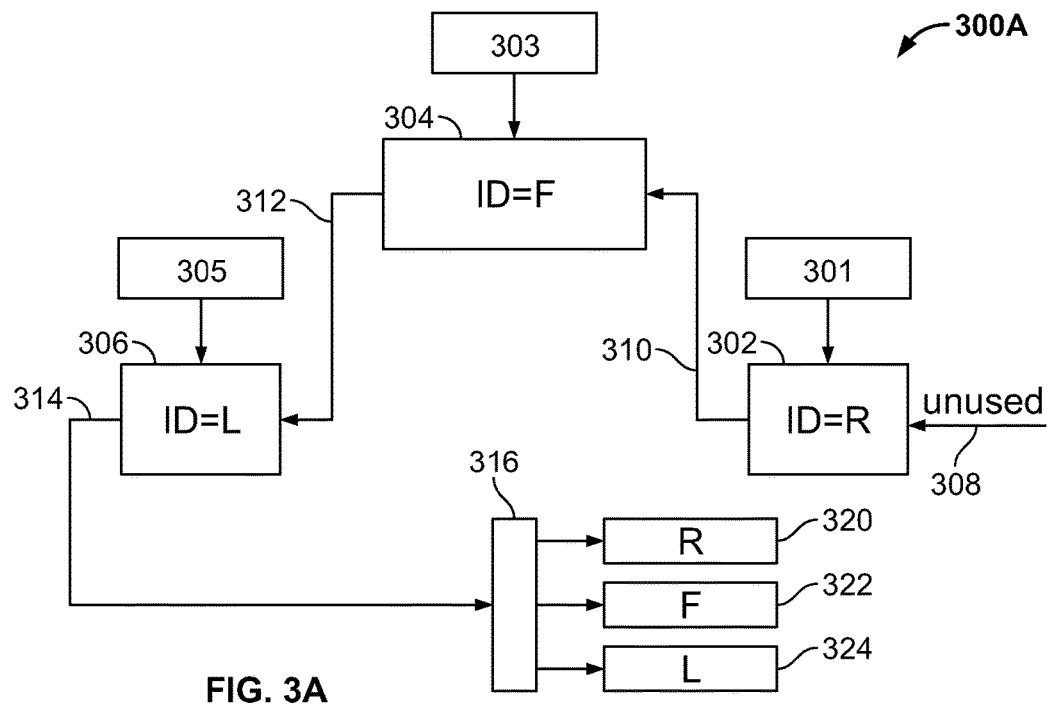
FIG. 3A is a block diagram of a daisy chained multiple sensor serial circuit system, according to certain embodiments of the present specification.

Reference is now made to FIG. 3A, which illustrates a daisy chain serial multiple sensor circuit system 300A, according to certain embodiments of the present specification. Daisy-chain serial multiple sensor circuit system 300A includes a first side pointing image sensor circuit 302 (right-R), a front pointing image sensor circuit 304 (front-F) and a second side pointing image sensor circuit 306 (left-L). Each image sensor circuit receives an input image from sensor array 301, 303 and 305 respectively.

FIG. 3A describes a chain of three sensors L←F←R. However, the number of sensors per chain can be two or more than three based on the system's requirements. Furthermore, the order of sensors within a chain, however hard-wired, may also vary, according to system constraints and requirements, for example: F←L←R.

According to embodiments of the present specification, image sensor circuits 302, 304 and 306 are daisy chained. The output of a serializer unit (similar to serializer 212 of FIG. 2) of the first side pointing image sensor circuit 302 is connected as input to a de-serializer (similar to the de-serializer 208 of FIG. 2) of the front pointing image sensor circuit 304 by a single serial PCB line 310. Similarly, the output of a serializer unit of the front pointing image sensor circuit 304 is connected as input to a de-serializer of the second side pointing image sensor circuit 306 by a single serial PCB line 312. The output of a serializer unit of the second side pointing circuit 306 is connected to a central control unit 316 by a single serial line 314 implemented as a cable (such as coax, twin-ax, twisted pair, etc.).

According to embodiments of the present specification, the daisy chain multiple sensor endoscope tip section image sensor circuits are used to transfer data to central control unit 316 over a single serial line 314.

According to embodiments of the present specification, each image sensor circuit 302, 304 and 306 is assigned with an exclusive identifier (ID) used to encode data from the first (right) side pointing sensor (ID=R) 302, data from front pointing image sensor (ID=F) 304 and data from second (left) side pointing sensor (ID=L) 306. Setting the ID of an image sensor circuit may be done by choosing the value(s) of resistor(s) connected to dedicated sensor ID pin(s) as illustrated in FIG. 2 (ID pin(s) 216). Alternatively, an image sensor circuit can be designed to automatically learn its place in the chain, by methods including, but not limited to: 1. examining the net bitrate at its input versus the total gross bitrate; or, 2. deducing it is a first in chain sensor if its input is inactive (308). If input is active, it detects what is the highest sensor number n whose packets were received at the input, then concludes its own number is n+1. The compression units may add headers to the video packets which may include, but are not limited to: 1. sensor ID; and, 2. time stamps and/or coordinate of a region within an image related to the packet. In various embodiments, the region is an entire line of pixels or a rectangle that encompasses a group of neighboring pixels (such as, for example, a 16×16 rectangle of pixels). Image sensor ID may be used to select interleaving schemes that may depend on the position of the image sensor circuit in the daisy chain as explained further herein below with reference to FIG. 4A and FIG. 4B. Image sensor ID is used by central control unit 316 to de-interleave the serialized video packets.

Central control unit 316 is configured to de-interleave the serial video packet stream received on single line 314 and to regenerate three separate and distinct displays R 320, F 322 and L 324 as captured by sensor arrays 301, 303 and 305 respectively.

According to certain embodiments of the present specification, the serial video packet stream transferred on single line 314 is boosted at the endoscope handle for example (not shown) before it is received and processed by central control unit 316. Digital signals are transmitted using an analog transmission scheme, and all signals are subject to degradation effects such as noise, distortion, and loss. Over short distances and at low bit rates, single line 314 may transmit the serialized video data with sufficient fidelity. However, at high bit rates and over longer distances, various effects may degrade the electrical signal to the point where errors may occur in the displayed images. Due to the length of single line 314 and optionally high data transfer rate that may be 0.1 to 10 Gigabit per second or more, a boost or amplification unit may be added to the endoscope tip or endoscope handle.

Figure 3B:
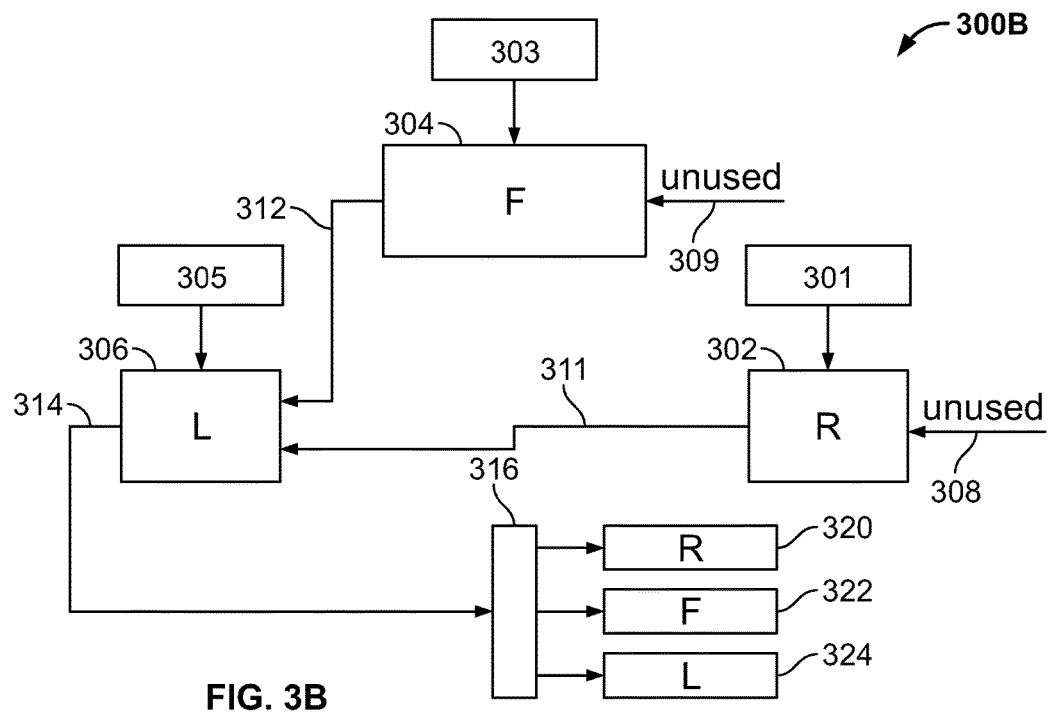
FIG. 3B is a block diagram of a daisy chained, parallel multiple sensor circuit system, according to certain embodiments of the present specification.

FIG. 3B illustrates another daisy chain multiple sensor circuit system 300B, according to certain embodiments of the present specification. The output of a serializer unit (similar to the serializer unit 212 of FIG. 2) of the right pointing circuit 302 is connected directly as an input to a de-serializer (similar to the de-serializer 208 of FIG. 2) of the left pointing circuit 306 by single serial line 311. Similarly, the output of a serializer unit of the front pointing circuit 304 is also connected as an input to the de-serializer of the left pointing circuit 306 by single serial line 312. The output of a serializer unit of the left pointing circuit 306 is connected to central control unit 316 by single serial line 314. In the parallel configuration illustrated in FIG. 3B, left pointing circuit 306 is a last-in-chain image sensor circuit, connected in parallel to previous image sensor circuits 302 and 304. Image sensor circuits 302 and 304 receive inactive inputs 308 and 309.

Central control unit 316 is configured to de-interleave the serial video packet stream received on single 314 and regenerate three separate and distinct images R 320, F 322 and L 324 as captured by sensor arrays 301, 303 and 305.

According to embodiments of the current specification, various interleaving schemes are used to interleave video packets using arbitration unit 210 of FIG. 2. Two non-limiting examples of such interleaving schemes are described below.

According to certain embodiments of the present specification, image sensor circuits 302, 304 and 306 may be connected directly, in parallel, to central control circuit 316. Each image sensor is configured to transfer data to central control unit 316 over a single serial line and central control circuit 316 is configured to receive and display the three separate images R 320, F 322 and L 324 as captured by sensor arrays 301, 303 and 305.

FIG. 4A illustrates a fixed rate interleaving data flow, according to certain embodiments of the present specification. Right pointing image sensor circuit 302 receives "k" Mbytes per second video data from image sensor 301 that captures the right FOV 103 of endoscope tip as shown in FIG. 1, where "k" may be 445 Mbytes per second, as described above, but generally "k" depends on the encoding pixel type, the compression ratio, the video mode, among other variables. According to the fixed rate interleaving data flow, an arbitration unit is configured to add two void video packets on each video packet received from sensor array 301 and to output the interleaved video packets over single serial line 310 to front pointing image sensor circuit 304. The serial output bit rate over line 310 is 3×K Mbits per second, where K is S times bigger than k due to byte to bits conversion. For example, when using 10:8 encoding, S equals 10. Using bytes as parallel words within the sensors is shown here merely as an example. An actual sensor may be designed to operate with parallel words of other sizes (for example, 16-bit, 32-bit and 64-bit words).

An exemplary calculation of the bitrate at the output of a daisy chain multiple sensor, according to certain embodiments of the present specification, for a system of three sensors in a daisy chain, working in interlaced video mode, using YCbCr 4:2:2 encoding, using 2:1 compression ratio, where every byte is transmitted as a 10-bit symbol (10:8 coding), at serial line 314 would be: 3×(½)×(⅔)×(½)×445 MB/Sec×10 Bit/Byte=2.23 Gigabits per second (GbpS). Alternately, considering a sensor with 800×800 resolution, 30 frames per second, 25% blanking overhead, 10 bit raw format, 8:10 coding, the bitrate for a chain of three sensors would be: 3×800×800×30×1.25×10×10/8=0.9 GbpS.

Front pointing image sensor circuit 304 receives k Mbytes per second video data from image sensor 303 that captures the front FOV 105 of endoscope tip as shown in FIG. 1. Additionally, front pointing image sensor circuit 304 receives 3K Mbits per second serial video data from right image sensor circuit 302 over single line 310. According to the fixed rate interleaving data flow, the arbitration unit is configured to draw two video packets (one is void, the other contains real video) from the chain packet buffer on each video packet it draws from the self-packet buffer and to output the interleaved video packets over single line 312 to left pointing image sensor circuit 306. The serial output data rate over line 312 is again 3K Mbits per second.

Alternatively, image sensor circuit 200 of FIG. 2 may be designed to avoid loading its chain packet buffer with ingress video packets and to generate void packets whenever needed at its serial output 209 (FIG. 2).

Left pointing image sensor circuit 306 receives k Mbytes per second video data from image sensor 305 that captures the left FOV 107 of endoscope tip as shown in FIG. 1.

Additionally, left pointing image sensor circuit 306 receives 3K Mbits per second serial video data from front image sensor circuit 304 over single serial line 312. The arbitration unit is configured to draw two video packets from the chain packet buffer on each video packet it draws from the self-packet buffer and to output the interleaved video packets over single serial line 314 to central control unit 316. The serial output data rate over line 314 is again 3K Mbits per second, however, with no (or very few) void packets.

In other words, in the fixed rate interleaving scheme, the arbitration unit is configured to draw and interleave video packets, alternately, one video packet from the self-packet buffer and two video packets from the chained packet buffer. In accordance with an embodiment, the plurality of daisy chained image sensors 301, 303 and 305 are also configured to capture image frames with identical frame rates. Alternately, the frame rates vary dynamically.

An advantage of the fixed rate interleaving scheme is that image sensor circuits 302, 304 and 306 process their input data almost identically and thus a single ASIC processor may be designed, fabricated and tested for the fixed rate interleaving. The fixed rate interleaving scheme requires writing real video data over void video data during processing. Referring to FIG. 4B below, a variable rate interleaving scheme is disclosed that requires designing a different data processing scheme for each image sensor circuit in the chain.

FIG. 4B illustrates a variable rate interleaving data flow, according to certain embodiments. Right pointing image sensor circuit 302 receives k Mbytes per second video data from image sensor 301 that captures the right FOV 103 of endoscope tip as shown in FIG. 1. According to the variable rate data flow, the arbitration unit is configured to output the stored video packets over single serial line 310 to front pointing image sensor circuit 304 as is. The serial output data rate over line 310 is 1K Mbits per second (for example: K=8*k, or K=10*k in 10:8 encoding).

Front pointing image sensor circuit 304 receives k Mbytes per second video data from image sensor 303 that captures the front FOV 105 of the endoscope tip as shown in FIG. 1. Additionally, front pointing image sensor circuit 304 receives K Mbits per second serial video data from right image sensor circuit 302 over single serial line 310. According to the variable rate interleaving data flow, the arbitration unit is configured to draw one video packet from the chain packet buffer on each video packet it draws from the self-packet buffer (not shown) and to output the interleaved video packets over a single serial line 312 to left pointing image sensor circuit 306. The serial output data rate over line 312 is 2K Mbits per second.

Left pointing image sensor circuit 306 receives k Mbytes per second video data from image sensor 305 that captures the left FOV 107 of the endoscope tip as shown in FIG. 1. Additionally, left pointing image sensor circuit 306 receives 2K Mbits per second serial video data from front image sensor circuit 304 over single line 312. According to the variable rate interleaving data flow, the arbitration unit is configured to draw two video packets from the chain packet buffer for each video packet it draws from the self-packet buffer and to output the interleaved video packets over single serial line 314 to central control unit 316. The serial output data rate over line 314 is 3 K Mbits per second.

In other words, in the variable rate interleaving scheme, the arbitration unit is configured to draw and interleave video packets, alternately, one video packet from the self-packet buffer and a variable number of video packets from the chained packet buffer. In accordance with an embodiment, the plurality of daisy chained image sensors 301, 303 and 305 are also configured to capture image frames with variable frame rates that depend on a position of an image sensor within the daisy chained image sensors. Alternately, the frame rates vary dynamically.

An advantage of the variable rate interleaving scheme described above is that no, or very slight, addition of void video packets by image sensor circuits 302 and 304 is required. A reduction in electromagnetic interference (EMI) emission and a lower power consumption resulting in less dissipated heat may also be advantageous. A single ASIC processor implementing image sensor circuit 200 may still be designed having multiple interleaving options that may be activated according to the image sensor circuit ID.

In an embodiment, the image sensor's frame rate depends on the position of the image sensor circuit in the chain and also varies dynamically.

In another embodiment, the image sensor's frame rate is configured to lock on the gross bitrate of ingress packets. In such an implementation, the first image sensor in chain is the only image sensor that generates bitrate independent of previous image sensors since it has no ingress video packets to lock on. The first image sensor egress packets dictate to the next image sensors in chain the gross bitrate. Then, by locking the frame rate on the ingress gross bitrate in each sensor in the chain, the first image sensor facilitates all sensors operating at the same frame rate and phase.

The image sensor circuit identifiers may be utilized by non-volatile memory cell technologies such as: programmable read only memory (PROM) cell technology; erasable programmable read only memory (EPROM) cell technology; electrically erasable programmable read only memory (EEPROM) cell technology; NVRAM technology, fuse cells and the like known in the art.

The image sensor circuit identifiers are utilized by connecting resistor(s) with well-defined values to sensor pin(s).

The image sensor circuit identifiers are utilized by automatic learning algorithms similar to the two examples described herein above.

In one embodiment, the image sensor circuit includes microelectromechanical systems (MEMS) sensors, accelerometers and/or gyros, for indicating the multiple sensor tip section temporal position and orientation in a patient's colon, for example.

In one embodiment, the image sensor circuit includes output pins to drive each of a plurality of LEDs with its own supply current, defined by the central control unit.

In an embodiment, the image sensor circuit includes an internal temperature sensor whose digital reading can be embedded inside video packets, and in turn be read by the central control unit.

Figure 5:
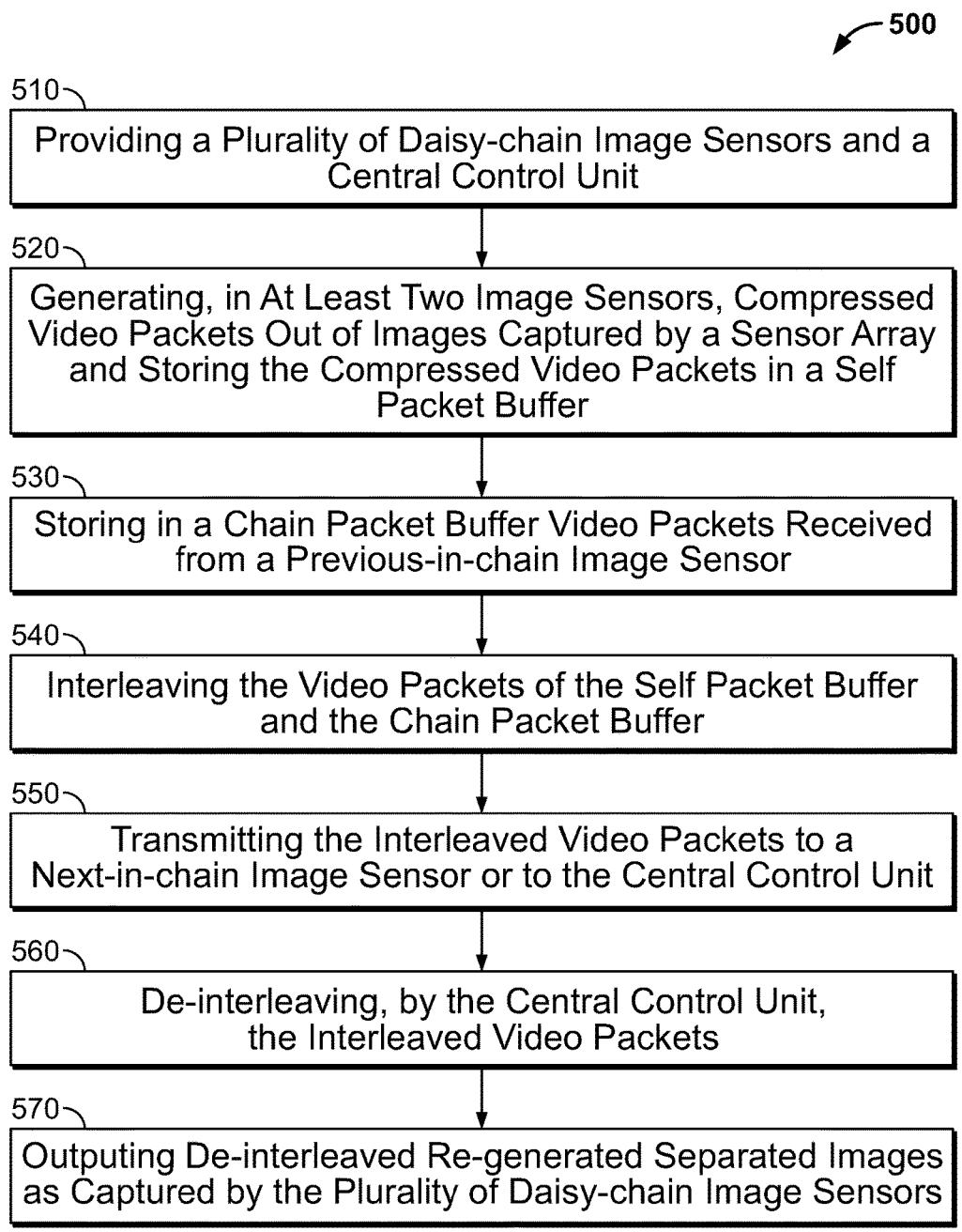
FIG. 5 is a flow chart describing a video processing method for a daisy chained multiple sensor endoscope, according to certain embodiments of the present specification.

FIG. 5 illustrates video processing method 500 for a daisy chain multiple sensor endoscope, according to certain embodiments of the present specification. Video processing method 500 includes: in stage 510, providing a multiple sensor endoscope comprising a plurality of daisy chain image sensors and a central control unit; in stage 520, generating, in each image sensor, video packets out of images captured by a sensor array, and storing, the optionally compressed, video packets in a self-packet buffer; in stage 530, storing, in a chain packet buffer, video packets received from previous-in-chain image sensors; in stage 540, interleaving the video packets drawn from the self-packet buffer and the chain packet buffer; in stage 550, transmitting the interleaved video packets to a next-in-chain image sensor or to the central control unit; in stage 560, de-interleaving, by the central control unit, the interleaved video packets; and in stage 570, outputting de-interleaved re-generated separated images as captured by the plurality of daisy chain image sensors.

Video processing method 500 stage 520 includes, in certain embodiments, compressing video packets with various compressing schemes and ratios known in the art.

Video processing method 500 stage 520 includes, in some embodiments, generating video packets with varying frame rate that depends on the position of the image sensor in the chain wherein the interleaving scheme of the video packets may vary accordingly.

Video processing method 500 stage 550 includes, in various embodiments, transmitting serial data with identical gross bitrate independent of the image sensor circuit position in the chain.

Video processing method 500 stage 550 includes, in various embodiments, transmitting serial data with variable bitrate that depends on the image sensor circuit position in the chain, wherein the serial output unit data transfer rate of an image sensor circuit is n+1 times the serial output unit data transfer rate of the previous-in-chain image sensor circuit, where n is the number of preceding image sensor circuits in the image sensor daisy chain.

Advantageously, the above described endoscope system, having a daisy chained multiple sensor configuration, may be used to display a plurality of images captured by a plurality of camera sensors disposed at an endoscope tip section where the plurality of images are transferred over a single line.

Another advantage of the above described endoscope system, having a daisy chained multiple sensor configuration, is that further miniaturization of the endoscope tip section may be achieved due to transferring video data over a single serial line. Alternatively, a wider working channel is enabled for insertion of surgery tools and larger illuminators, optical lens systems and sensor arrays may be utilized, taking advantage of the single serial line transmission.

Another advantage of the above described endoscope system, having a daisy chained multiple sensor configuration, is that a single ASIC that performs almost identical data processing in the plurality of image sensor circuits may be designed, fabricated and tested.

Another advantage of the above described endoscope system, having a daisy chained multiple sensor configuration, is that the image sensor's frame rate may depend on the position of the image sensor in the chain and may also vary dynamically.

Another advantage of the above described endoscope system, having a daisy chained multiple sensor configuration, is that transmission over a single serial line prevents the risk of cross talk between adjacent high-speed serial lines.

Another advantage of the above described endoscope system, having a daisy chained multi-sensor configuration, is that it minimizes the complexity of the endoscope tip flexible board design by reducing the number of wires required to interconnect image sensors.

In accordance with another embodiment, the present specification discloses parallel illuminating systems that allow regulation of each illuminator's illumination intensity independently. Regulating each illuminator's illumination intensity allows illuminating different orientations with different illumination intensities during a colonoscopy procedure, for example. Regulating each illuminator's illumination intensity may prevent dazzling from the cameras' sensor arrays due to light reflection from near walls, and on the other hand, may prevent displaying too dark screens due to weak illumination intensities in other directions.

Furthermore, regulating each illuminator's illumination intensity may reduce the overall power consumption of the endoscope and thus may reduce heat production in the endoscope's tip section.

Another advantage of regulating each illuminator's illumination intensity independently is that different types of illuminators may be switched on or switched off on demand. For example, illuminators may be specific blue and green wavelength range LEDs implementing a narrow band imaging technique, where the light of the specific blue and green wavelengths is used to enhance the detail of certain aspects of the surface of a mucosa, when needed.

According to aspects of the present specification, parallel illuminating systems and illumination methods are disclosed. The system includes at least one viewing element or camera sensor configured to capture images and at least two illuminators connected in parallel to a power supply line and configured to illuminate a plurality of FOVs. Each one of the at least two illuminators further comprises a control circuit configured to control the illuminator's illumination intensity according to control signals generated by a central control circuit's processor. While the present specification describes an endoscope with respect to the use of multiple cameras, it should be noted that the disclosure may be applied, in various embodiments, to multiple viewing elements.

According to certain embodiments of the present specification, the endoscope may be a colonoscope, a gastroscope, a laparoscope, an arthroscope, a thoracoscope and the like.

In an embodiment, at least one control signal generated by the central control circuit's processor may carry instructions for a plurality of LEDs connected in parallel, and thus may regulate the illumination intensity of each illuminator dynamically independent from other illuminators. The at least one control signal may comprise instructions for switching on and off each illuminator independent from other illuminators under a specific parallel connection and for varying the intensities of each illuminator independently.

In an embodiment, the control signal and power supply may be combined and provided to the illuminators over a single line where the illuminators may be connected in parallel to the same line carrying both power and instructions. Alternatively, the control signal (i.e. instructions) and power supply may be provided to each illuminator on separate lines.

In an embodiment, the central control circuit's processor may be configured to encode control signal (instructions) and transmit the encoded instructions to the illuminators wherein each illuminator's control circuit may be configured to decode the encoded instructions received from the central control circuit's processor.

In an embodiment, the illuminators may be used to transmit information from the endoscope's tip section back to the central control circuit's processor as a part of a telemetry system.

In an embodiment, encoded control signal instructions may comprise instructions for varying the electric current flow through each illuminator.

In an embodiment, encoded control signal instructions may be communicated over the power line using a serial protocol such as, but not limited to, universal-asynchronous-receiver-transmitter (UART) protocol. The encoded control signal instructions may comprise illuminator IDs wherein illuminators' control circuits may be configured to decode the encoded illuminators' IDs and regulate illumination intensity accordingly.

In an embodiment, the central control circuit's processor may be configured to vary an illumination intensity of each illuminator automatically using an image processing software program code or hardware circuit. The image processing software program code or hardware circuit may be configured to detect high intensity reflections received by camera sensor arrays and decrease the illumination intensity of at least one illuminator accordingly.

In an embodiment, the image processing software program code or hardware circuit may be configured to detect weak intensity reflections received by camera sensor arrays and increase the illumination intensity of at least one illuminator accordingly.

In an embodiment, the central control circuit's processor may be configured to vary the illuminators' illumination intensity according to surgeons' manual operations via a user interface.

In an embodiment, the illuminators comprise light emitting diodes (LEDs) wherein the illuminators' control circuits comprise circuits used to control the currents that flow through each LED.

In an embodiment, a maximal upper bound allowed current through each one of the plurality of LEDs may be used to prevent overheating an LED or the endoscope's tip section, where the central control circuit's processor may be configured to reduce currents in one or more LEDs accordingly.

In an embodiment, one or more illuminators may have a different light wavelength range comparing to other illuminators' light wavelength ranges. Typical wavelength of illuminators may be in the visible wavelength ranges and one or more illuminators wavelength may be in the infra-red (IR), close IR or a specific blue or green wavelength for example for an NBI system.

In an embodiment, the illuminators' control circuit processors may be implemented as application specific integrated circuits (ASICs). However, other processor types, such as field programmable gate arrays (FPGAs), and the like, are in the scope and may be used in certain embodiments of the present invention.

In an embodiment, each illuminator may include more than one LED, connected serially in a chain or in a parallel configuration.

According to certain embodiments of the present specification, the illuminators may be hybrid systems that include an FPGA and a LED, an ASIC and LED, an ASIC of two or more LEDs and their logic, an ASIC containing only logic with pads on its upper side configured to be mounted to a LED, and combinations of thereof.

Figure 6:
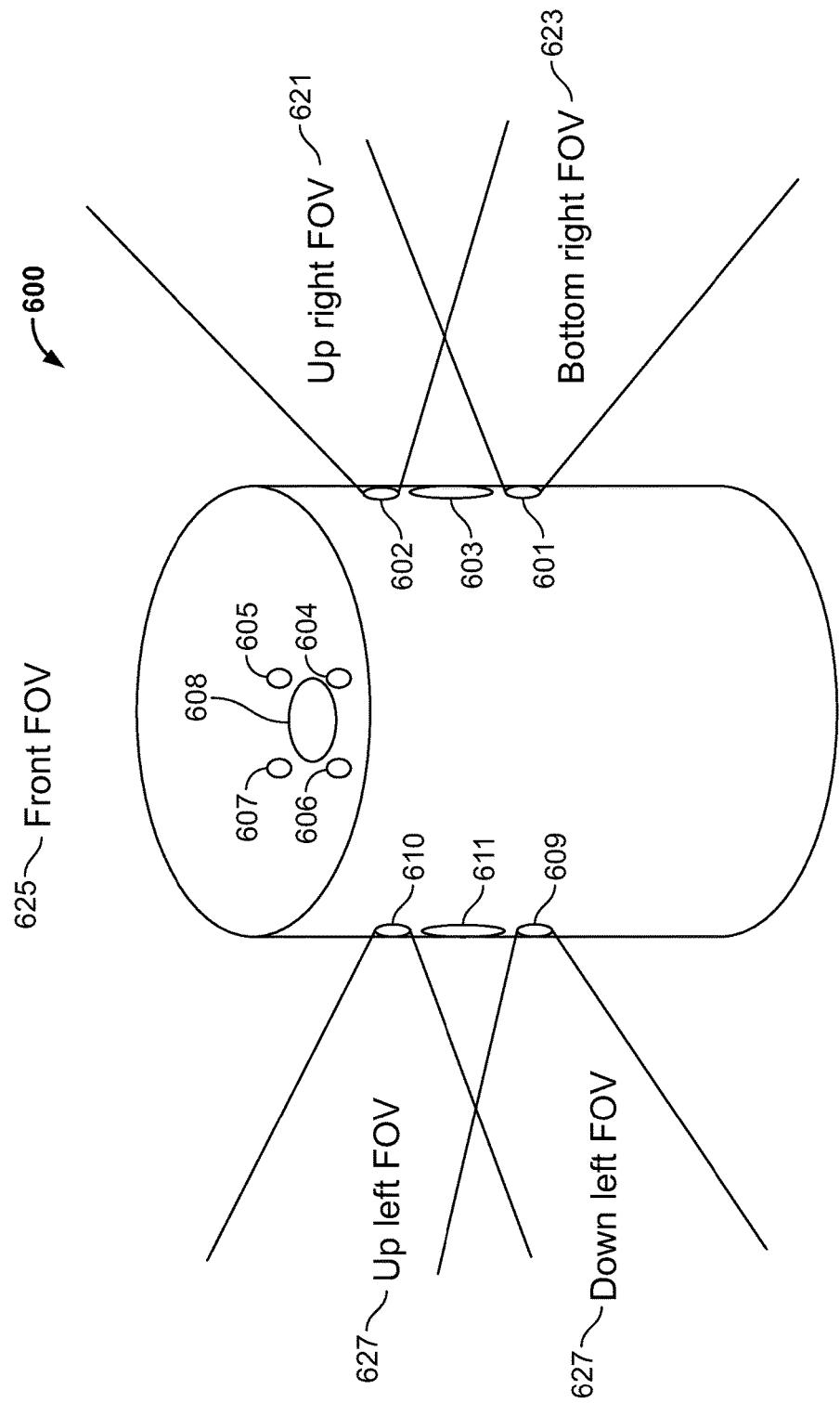
FIG. 6 illustrates an exemplary tip section of an endoscope that includes a plurality of cameras and parallel illuminating systems, according to certain embodiments of the present specification.

Reference is now made to FIG. 6, which illustrates an exemplary endoscope tip section comprising a plurality of multiple viewing elements and a parallel illuminating system, according to certain embodiments. Endoscope tip section's parallel illuminating system 600 includes a side pointing camera sensor 603 and two side pointing illuminators 601 and 602, illuminating an upper right FOV 621 and a lower right FOV 623. Endoscope tip parallel illuminating system 600 includes a front pointing camera sensor 608 and four front pointing illuminators 604, 605, 606 and 607, which illuminate a front FOV 625. Endoscope tip parallel illuminating system 600 includes another side pointing camera sensor 611 and two side pointing illuminators 609 and 610, which illuminate a lower left FOV and an upper left FOV, respectively, creating a left FOV 627.

In accordance with various embodiments, camera sensors 603, 608 and 611 are CCD arrays or CMOS arrays.

It is further understood that the endoscope tip section includes a working channel (as shown in FIG. 1, for example) configured to inject fluids or gases and to insert miniscule surgery tools, a plurality of optical systems that may include front and side objective lens systems, a flexible electronic circuit board configured to carry the front and side camera sensors, the wiring connections between these components and a cable connecting endoscope tip section's parallel illuminating system 600 to an endoscope handle, to an external control unit and to a display.

The endoscope tip section's parallel illuminating system 600 illustrated in FIG. 6 and further described in details below, is a non-limiting example of a parallel illuminating system. According to other embodiments of the present invention, similar parallel illuminating systems may be used in automotive industry, large display screens, in office and home illuminating systems and the like.

Figure 7:
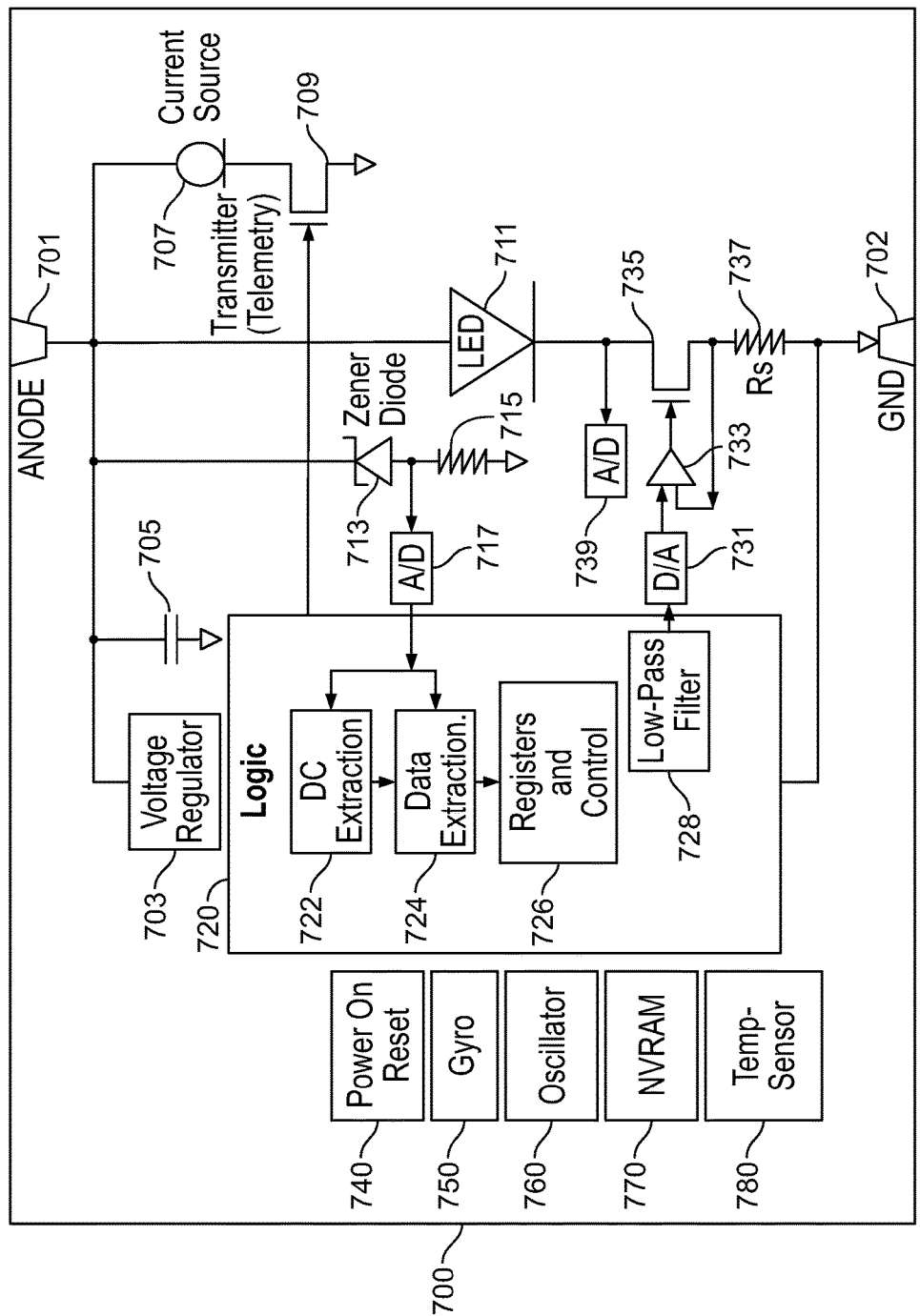
FIG. 7 is a block diagram illustrating an illuminator circuit, according to certain embodiments of the present specification.

Reference is now made to FIG. 7, which illustrates an illuminator circuit in a block diagram, according to certain embodiments. Illuminator circuit 700 includes a power supply input pin ANODE 701 on which a control signal is superimposed and a ground input pin GND 702. ANODE pin 701 is in electrical communication with or connected to voltage regulator 703, capacitor 705, Zener diode 713, current source 707 connected further to n-channel transistor 709. Zener diode 713 is in electrical communication with or connected to resistor 715 and to analog-to-digital (A/D) converter 717. Logic circuit 720 receives A/D's 717 digitized output signal, and comprises a DC extraction module 722, a data extraction module 724 and a registers and control module 726. Logic circuit 720 is configured to extract the inputted power supply DC level by DC extraction module 722 and to decode control signal instructions by data extraction module 724.

In various embodiments, data extraction module/circuit 724 includes a UART (universal-asynchronous-receiver-transmitter) decoder that is used to decode communicated UART instructions transmitted over power line (FIG. 8A 850) connected to input pin ANODE 701. In an embodiment, the UART protocol is a UART 9,600 bits per second protocol, includes a start bit, 1 even parity bit and 1 stop bit added to each transmitted byte.

According to embodiments of the present specification, the first UART communicated byte is an illuminator device ID, where LSB=1 encodes a UART read instruction and LSB=0 encodes a UART write instruction. The second communicated byte is a 4 bit LED-enable bits and the remaining 4 bits is an accessed register address. The third communicated byte is a data byte and the fourth communicated byte is a checksum byte. Accordingly, total number of bits transmitted per one UART instruction is 44 bits. Transmitting a 44 bits UART instruction lasts 4.5 milliseconds, where 104 micro seconds is a 1 bit transmission time duration of a UART 9,600 protocol.

In an embodiment, logic circuit 720 is implemented as an ASIC processor. However, other processor types, such as field programmable gate arrays (FPGAs), and the like, are in the scope and may be used in certain embodiments of the present specification. According to certain embodiments of the present specification, logic circuit 720 is implemented by a miniature FPGA (for example, 1.5 mm×1.5 mm FPGAs, or less, including the package are already available).

Logic circuit 720 is configured to generate a digitized control value decoded by the UART decoder and used to determine the desired current flow through LED 711. In this example, the illuminator circuit contains just a single LED. However, in other embodiments, illuminator circuit may contain more than one LED. The digitized control value is filtered using a low pass filter logic module 728 before it is converted to an analog signal by digital-to-analog (D/A) converter 731 and is inputted to operational-amplifier (Op-Amp) 733 non-inverting input. Low-pass filter 728 is used for soft-start switching on and off LED's 711 current gradually, minimize voltage under/over-shoot on power supply pin 701 while LED's 711 current is changing.

Op-Amp 733 output is connected to the gate of an n-channel field-effect transistor (FET) 735, whose source is connected to the inverting (feedback) input of Op-Amp 733. A drain for FET 735 is connected to a cathode of LED 711 and its source to resistor (Rs) 737. The illumination intensity, i.e. electric current flow, of LED 711 is practically identical to that of Rs 737. This electric current flow is controlled by Op-Amp 733 by means of feedback: Op-Amp 733 sets its output (hence, FET 735 gate node) to such a voltage, that the resulting voltage at its inverting (feedback) input is identical to that of its non-inverting input which is the extracted control signal UART instruction. Hence, the resulting electric current that flows through FET 735 and LED 711 is configured to be the desired UART instruction's voltage divided by the resistance of Rs 737.

According to certain embodiments, UART protocol is used to communicate control signal instructions over power line 850 (FIG. 8A) as described above. However, other standard or non-standard communication protocols, such as the serial peripheral interface (SPI) protocol, may be used to communicate control signals over power line 850 (FIG. 8A) in other embodiments of the present invention and are in the scope.

According to certain embodiments, UART write instructions are transmitted in broadcast mode, i.e. addressing a plurality of illuminators simultaneously, and/or allowing a multiple number of LEDs to be turned on or off simultaneously.

According to certain, power line communication (PLC) known techniques, adapted to DC power, are used to modulate UART, or other communication protocol that may be used.

In one embodiment, the illuminator circuit 700 includes power-on-reset module 740 configured to reset logic 720 to a known state upon power up.

In one embodiment, the illuminator circuit 700 includes motion sensor 750 that may be a gyro and/or an accelerometer configured to measure or maintain orientation of endoscope tip section 600 of FIG. 6.

In one embodiment, the illuminator circuit 700 includes oscillator 760 configured to generate internal clock signal for illuminator circuit 700. Frequency of oscillator 760 may be, for example, in the range of 500 KHz to 1 MHz.

In one embodiment, the illuminator circuit 700 includes non-volatile memory cells (NVRAM) 770 configured to store digital data such as: device parameters; illuminator part number; illuminator vendor ID; illuminator ID; records of operational hours per current range.

In one embodiment, temperature sensor 780 is configured to measure the illuminator junction temperature at a plurality of junctions in illuminator circuit 700, from which the endoscope tip section's equivalent temperature may be calculated.

In one embodiment, FET 709 switches current source 707 (with optional soft-start), to transmit telemetry data back to processor 810 (FIGS. 8A, 8B), in response to processor's 810 (FIGS. 8A, 8B) instructions.

In one embodiment, A/D 739 is configured to tap FET's 735 drain, such that processor 810 (FIGS. 8A, 8B), in response to a read request instruction, may be configured to determine if ANODE 701 voltage is within a desired range (i.e. FET 735 drain voltage is high enough such that FET 735 functions as a current regulator, and not too high, such that FET 735 overheats illuminator circuit 700).

Figure 8A:
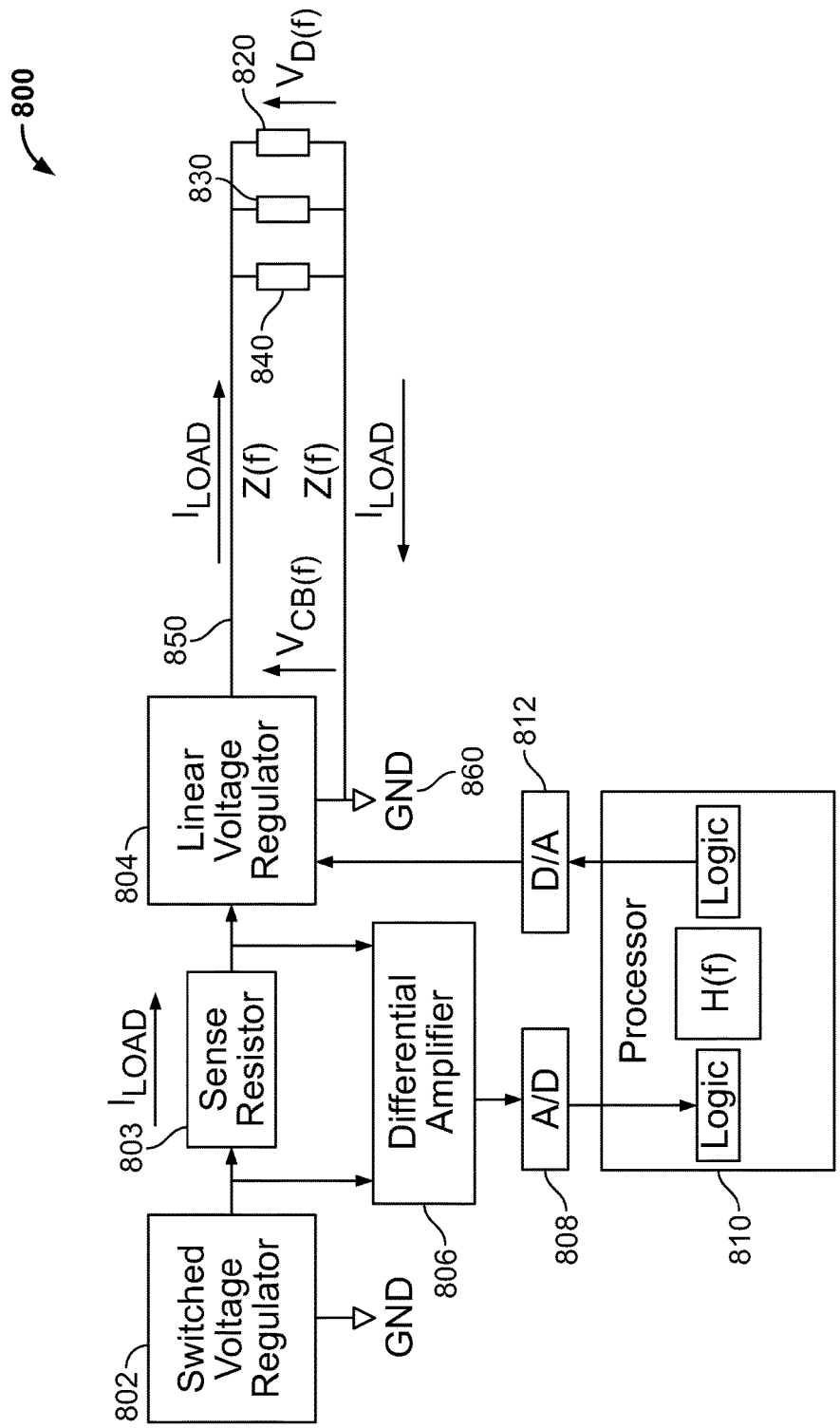
FIG. 8A is a parallel illuminating system circuit diagram, according to certain embodiments of the present specification.

In one embodiment, illuminator circuit 700 includes a third input pin (not shown in FIG. 7) used to communicate instructions not superimposed on power line 850 (FIG. 8A).

Reference is now made to FIG. 8A, which illustrates a parallel illuminating system circuit, according to certain embodiments. Parallel illuminating system circuit 800 includes switched voltage regulator 802 current sense resistor 803, linear voltage regulator 804, differential amplifier 806, A/D converter 808, D/A converter 812 and processor 810. FIG. 8A is an example, in which the parallel illuminating system circuit 800 includes three illuminator circuits 820, 830 and 840 connected to single line 850. However, in actual systems the number of illuminator circuits connected to a single line may be substantially higher.

Single power supply line 850 is a camera board (CB) power supply line of an endoscope. Typically, endoscope's CB power supply line may be 3 to 4 meters long, and may carry typically 40 mA current flow per illuminator in regular (yet maximal) illumination conditions, and 150 mA current flow per illuminator in flash illumination mode.

In one embodiment, the central control circuit processor 810 is a camera board (CB) circuit processor located at external control unit (not shown) connected to the endoscope and to a display or in the endoscope handle (not shown).

Illuminator circuits 820, 830 and 840 is the illuminator circuit illustrated and described with respect to FIG. 7 above where power line 850 is connected to FIG. 7 input pin ANODE 701 and GND 860 is connected to FIG. 7 input pin GND 702 for each illuminator circuit 820, 830 and 840. Processor 810 may be an FPGA, an ASIC, a software-controlled processor and the like. Processor 810 is configured to generate control signal instructions in order to vary the illumination intensity of each illuminator 820, 830 and 840 connected in parallel to power line 850. Processor 810 switches on or off each illuminator and regulates the illumination intensity of each illuminator independent from the operating condition of other illuminators. Processor 810 is configured to generate control signal instructions to illuminators 820, 830 and 840 automatically according to image processing of camera sensor arrays (603, 608 and 611 of FIG. 6) captured images. Processor 810 is configured to perform image processing by executing an image processing software program code stored in the processor memory (not shown). Alternatively, processor 810 may include an image processing hardware circuit.

The image processing program code is configured to detect high intensity reflections received by one or more camera sensors 603, 608 and 611 of FIG. 6 and reduces the illumination intensity of one or more illuminator circuits 820, 830 and 840 accordingly. The image processing program is configured to detect low intensity reflections received by one or more camera sensors 603, 608 and 611 of FIG. 6 and increases the illumination intensity of one or more illuminator circuits 820, 830 and 840 accordingly.

Additionally or alternatively, central control circuit's processor 810 is configured to vary the illumination intensity of illuminators 820, 830 and 840 according to manual instructions of a surgeon via a user interface (not shown).

In one embodiment, processor 810 is configured to regulate the illumination intensity of illuminators 820, 830 and 840 according to the endoscope tip section's temperature calculated by measuring the temperature at the illuminator junction (using temperature sensor 780 as shown in FIG. 7).

In one embodiment, processor 810 is configured to regulate the illumination intensity of illuminators 820, 830 and 840 according to motion sensor 750 (FIG. 7) indications. Motion sensor 750 may be a Micro Electro-Mechanical System (MEMS) accelerometer or gyro.

In one embodiment, processor 810 is configured to switch on and off illuminators allocated to special operational modes, for example NBI.

In one embodiment, processor 810 uses the output of A/D 808 to calculate the current flowing through power line 850 (i.e. load current), as part of built-in test (BIT) module whose purpose is to verify that each illuminator draws the current it is configured to draw.

In one embodiment, processor 810 uses the output of A/D 808 to calculate the current flowing through power line 850 (i.e. load current), and then increase the output VCB of the Line Voltage Regulator 804 to compensate for the voltage drops caused by power line's 850 resistance and the load current. This method of compensation is only effective if the processor 810 knows in advance what the resistance of power line 850 is.

In one embodiment, processor 810 is informed by the central control unit about the power line 850 resistance, after the central control unit queried the newly inserted endoscope about its type.

In one embodiment, processor 810 is configured to calculate the actual resistance of power line 850, by reading from the illuminators their power supply (ANODE 701 of FIG. 7) voltage. Accordingly, the difference between the desired VCB and the illuminators' supply voltage, divided by the current measured by the Sense Resistor (803) and converted by A/D (808) is the actual resistance.

According to embodiments of the present specification, more than one parallel illuminating system circuit, described in FIG. 8A hereinabove, may be implemented in parallel illuminating system 600 shown in FIG. 6, for example, reducing the current load from the power line and increasing the communication throughput.

Figure 8B:
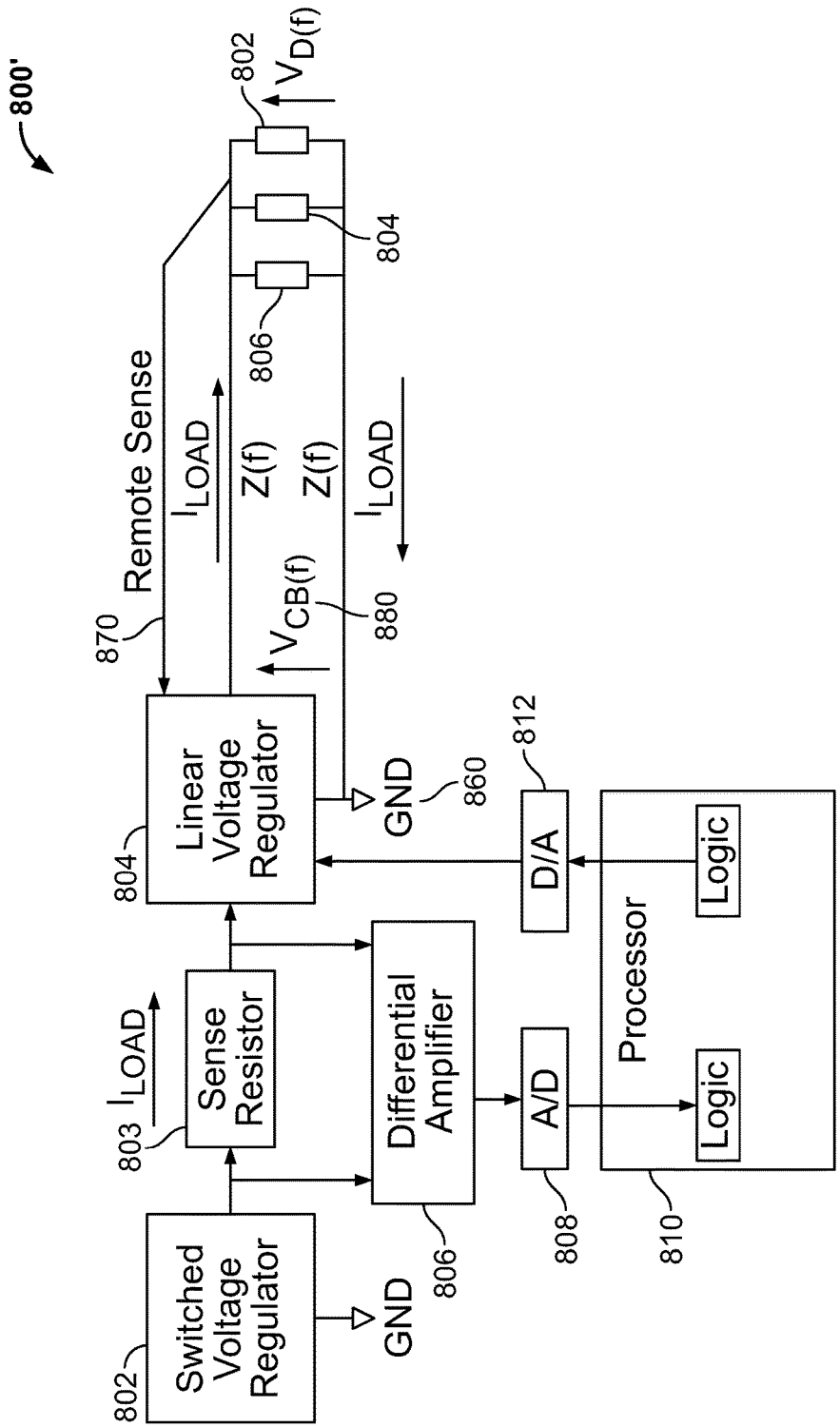
FIG. 8B illustrates the parallel illuminating system circuit diagram of FIG. 8A further incorporating a remote sense, according to certain embodiments.

Reference is now made to FIG. 8B, which illustrates the parallel illuminating system of FIG. 8A further incorporating a remote sense, according to certain embodiments. Parallel illuminating system circuit 800' includes remote sense line 870. Remote sense line 870 is configured to provide a measure of the actual voltage applied on the illuminators circuit inputs in order to provide desired operation condition. Remote sense line 870 is configured to detect a voltage fall, due to supply line's 850 load, and processor 810 is configured to compensate the voltage fall by increasing the applied voltage VCB 880.

Figure 9:
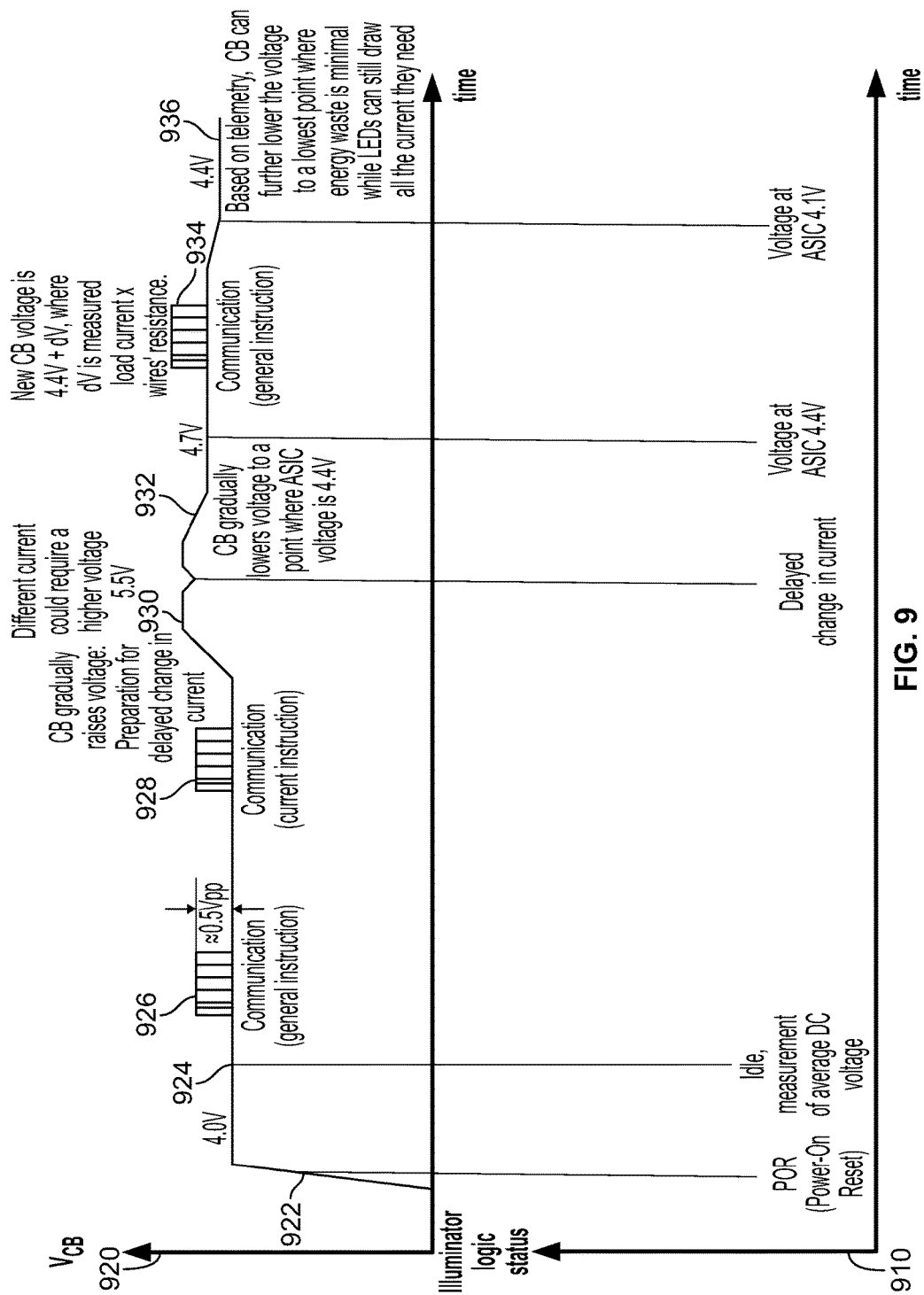
FIG. 9 is a schematic of transmission of control signal instructions over a camera board power supply line, according to certain embodiments of the present specification.

Reference is now made to FIG. 9 (along with FIGS. 7, 8A and 8B), which illustrates transmission of control signal instructions over a camera board (CB) power supply line, according to certain embodiments. Illuminator's logic status 910 and CB power supply line voltage VCB 920 are illustrated in FIG. 9. During power-on-reset (POR) procedure 922, processor 810 (shown in FIG. 8B) is configured to increase the applied voltage VCB from 0.0 Volts to 4.0 Volts (shown as 880 in FIG. 8B) monotonously, in a rate fast enough to cause a power on reset in the illuminators. Processor 810 is configured to idle for a while, so the illuminator can measure the average idle DC voltage 924 using A/D 717. Processor 810 is configured to communicate control signal instructions 926 over CB power line 850. Control signal instructions 926 is general UART instructions that include read or write bit, register address bits and data bits. Device identification bits are used to encode illuminator IDs for example. Processor 810 is configured to communicate control signal instruction 928 that is used to encode the desired current flow through RS resistor 737 (shown in FIG. 7) for each illuminator, which determines the illumination intensity of LED 711 (shown in FIG. 7) for each illuminator circuit 820, 830 and 840. A/D 717 is configured to measure continuously the illuminators voltage at ANODE 701 while processor 810 is idle, and calculate its average (low-pass filtering) to extract the power line DC level in the DC Extraction module 722. Data Extraction 724 module monitors if ANODE 701 voltage rises from DC+160 mV (exemplary value) to DC+320 mV (exemplary value) fast enough (i.e. slew rate must exceed a threshold). If it does exceed the threshold, logic 720 deduces that processor 810 transmitted a '0' bit (according to UART protocol, '0' has a higher voltage than '1'. Also, logic state while in idle is '1'). Similarly, if ANODE 701 voltage falls from DC+320 mV to DC+160 mV fast enough, logic 720 deduces that the processor 810 transmitted a '1' bit.

The three illuminators circuits 820, 830 and 840 are an exemplary parallel illuminating system only. Any other number of illuminators may be used according to embodiments of the present specification.

The exemplary instruction 928 shown is one that results in one or more illuminators changing their current (light intensity). Therefore, processor 810 increases the applied voltage VCB to 5.5V 930 to immune the power line against a scenario where a sudden and sharp increase in illuminator current would drop ANODE 701 voltage to a value causing unintentional power on reset in illuminators' logic or a temporary flicker. Since VCB's rise 930 to 5.5V is slow, it is not interpreted by the illuminators as a logic '0' transmission. Between 930 and 932, the illuminator(s) update its (their) current according to instruction 928. The updating of current occurs after an intentional delay, meant to guarantee VCB has completed reaching the exemplary voltage 5.5V 930. Processor 810 is configured to gradually decrease the applied voltage VCB to 4.7V 932, where 4.4V may be the voltage applied onto illuminators' ANODE 701 in this example. (the 300 mV difference between VCB and Anodes' voltages is due to power line resistance). While 4.4V at the ANODE 701 does guarantee correct operation of logic 720 and Op-Amp 733 circuits, a lower voltage may be preferred, to minimize illuminators' power consumption.

Processor 810 is configured to communicate another control signal instruction 934 over CB power line 850. Control signal instruction 934 is used, for example, to reduce the illumination intensity of one or more illuminators, to increase the illumination intensity of one or more illuminators (in cases where VCB rise 930 is not mandatory), to switch on or switch off one or more illuminators, configure illuminators, and/or read data from an illuminator.

Processor 810 may start a phase 936 of fine tuning, i.e. reading from the illuminators their ANODE 701 voltage and FET's 735 drain voltage and lowering VCB to a point where these voltages suffice, yet are low enough to ensure minimal heat dissipation.

Figure 10:
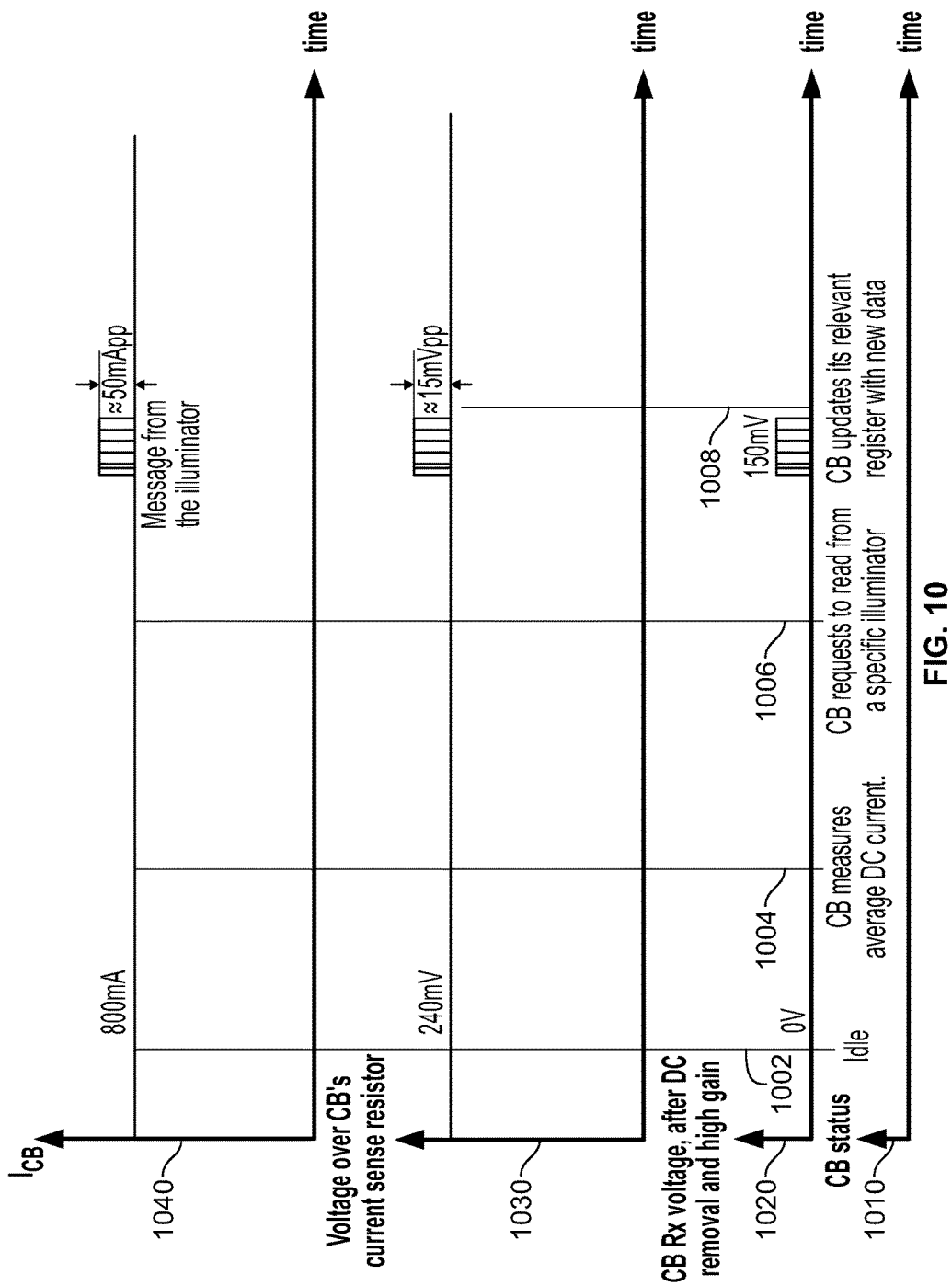
FIG. 10 is a schematic of a camera board supply line status, voltage and current, according to certain embodiments of the present specification.

Reference is now made to FIG. 10 (along with FIGS. 7, 8A and 8B), which illustrates the camera board power supply line status 1010, voltage 1030 across, and current 1040 through the Sense Resistor 803, according to certain embodiments. CB power supply line status 1010 may be idle 1002, may be measuring average DC current 1004, may be sending a read request to an illuminator's processor register 1006 and may be updating its internal register(s) with new data 1008 received from the illuminator, for example.

The operations illustrated in FIG. 10 are exemplary operations only and other operations may be implemented in embodiments of the present specification and are in the scope of the present specification.

In CB power line idle state 1002, the average DC voltage fall over the current sense resistor 803 may be 240 mV (assuming exemplary sense resistor value of 0.3 Ohm and DC load current of 800 mA) and the average current ICB may be 800 mA, for example, as shown in FIG. 10.

After processor 810 has calculated the average DC load current 1004, it is allowed to, and may send, a request 1006 to an illuminator to transmit data. It then waits for the illuminator to transmit the requested data. As the illuminator transmits data, the illuminator transmits a '0' by switching on its internal ~50 mA current source especially allocated for telemetry (707, 709). When this current source is off, it is equivalent to illuminator transmitting a '1'. As a result, the load current 1040, as well as the voltage across the sense resistor 1030, take the form of a DC value on which small perturbations (which are in fact the data transmitted from the illuminator) are superimposed.

Hardware on the CB is configured to extract the above-mentioned perturbations by first removing the DC value (already calculated in 1004), then amplifying it by 10 (exemplary value) so it can better drive a comparator—which in turn will drive processor 810. This power line voltage and current after DC levels removal are shown during update of processor's 810 register with new data 1008. The maximal amplitude of the CB Rx Voltage (1020) is about 150 mV, the amplitude of the voltage developed on the current sense resistor is about 15 mV 1030 and the CB current ICB is 50 mA 1040 above DC voltage as shown in FIG. 10.

In one embodiment, 2 or more than 3 illuminators may be connected to CB power line 850. A parallel illuminating system having 8 illuminators is shown in FIG. 6 for example. Other number of illuminators connected in parallel and any number of independent chains of parallel-connected illuminators may be designed according to certain embodiments of the present specification.

In one embodiment, illuminator circuit processor 720 of FIG. 7 includes a watch-dog circuit (not shown). The watch-dog circuit sets a programmable counter configured to start counting every time a legitimate control signal instruction is received. If the counter reaches a pre-programmed value and a legitimate UART instruction was not received, the watch-dog circuit is configured to set the LED illumination level to a mid-range illumination intensity as a safety fallback.

Figure 11:
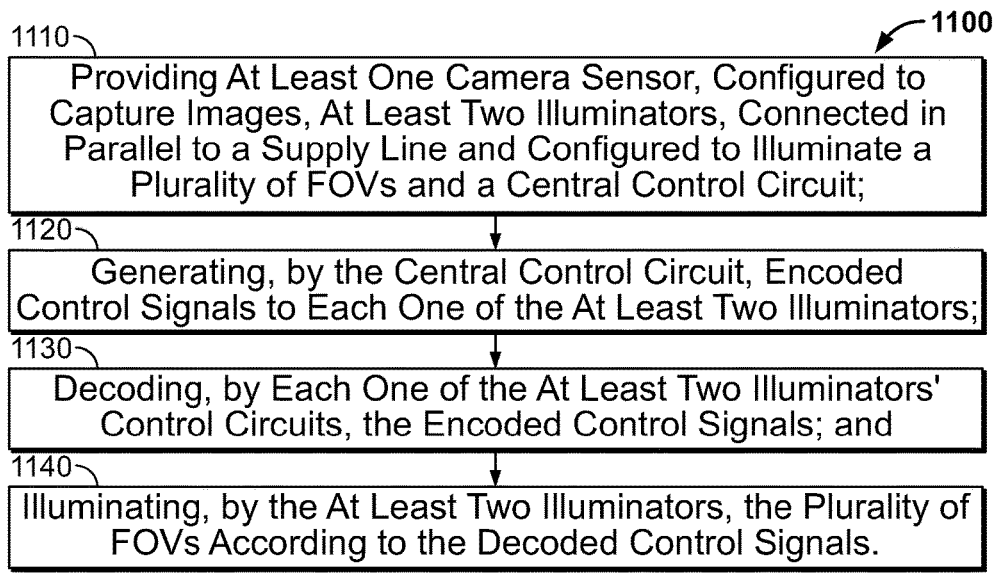
FIG. 11 is a flow diagram of an illumination method for a parallel illuminating system, according to certain embodiments of the present specification; and, FIG. 12 is a flow diagram of an illumination method for a parallel illuminating system, according to other certain embodiment of the present specification.

Reference is now made to FIG. 11, which illustrates an illumination method for a parallel illuminating system, according to certain embodiments. Illumination method 1100 includes: in stage 1110, providing at least one camera sensor configured to capture images, at least two illuminators connected in parallel to a power supply line and configured to illuminate a plurality of FOVs and a central control circuit; in stage 1120, generating, by the central control circuit, encoded control signals to each one of the at least two illuminators, or common encoded control signal to the at least two illuminators; in stage 1130, decoding, by each one of the at least two illuminators' control circuits, the encoded control signals; and in stage 1140, illuminating, by the at least two illuminators, the plurality of FOVs according to the decoded control signals.

In an embodiment, illumination method 1100 includes switching on and switching off each one of the illuminators independently.

In an embodiment, illumination method 1100 includes varying the illumination intensity of each illuminator independently.

In an embodiment, illumination method 700 includes transmitting encoded control signal instructions and power to the illuminators on a single power line 850 of FIG. 8A.

In an embodiment, illumination method 700 includes transmitting a UART protocol encoded instructions over power line 850 of FIG. 8A.

Figure 12:
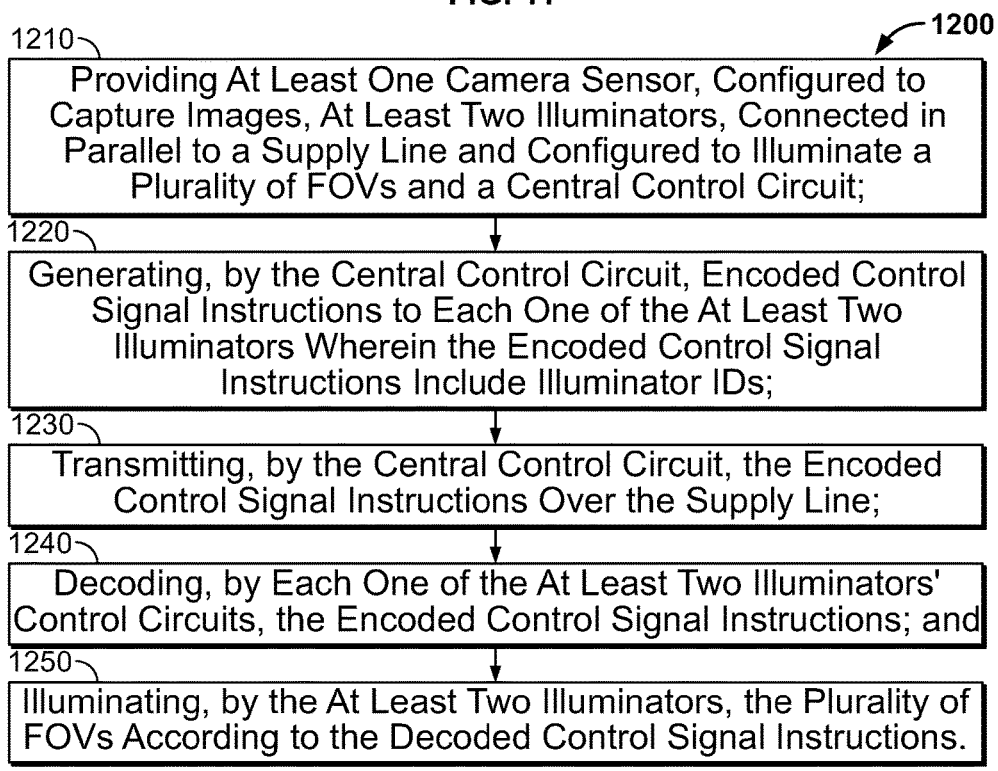

Reference is now made to FIG. 12, which illustrates an illumination method for a parallel illuminating system, according to other certain embodiments. Illumination method 1200 includes: in stage 1210, providing at least one camera sensor, configured to capture images, at least two illuminators, connected in parallel to a power supply line and configured to illuminate a plurality of FOVs and a central control circuit; in stage 1220, generating, by the central control circuit, encoded control signal instructions to each one of the at least two illuminators wherein the encoded control signal instructions include illuminator IDs; in stage 1230, transmitting, by the central control circuit, the encoded control signal instructions over the power supply line; in stage 1240, decoding, by each one of the at least two illuminators' control circuits, the encoded control signal instructions; and; in stage 1250, illuminating, by the at least two illuminators, the FOVs according to the decoded control signal instructions.

Advantageously, the above described parallel illuminating system is used to regulate illumination intensities of a multiple sensor endoscope having a plurality of illuminators at the endoscope's tip section, such as the tip section 600 of FIG. 6.

Another advantage of the above described parallel illuminating system is that control signals, such as UART instructions, and power are provided to illuminators on a single power line.

Another advantage of the above described parallel illuminating system is that UART protocol is used to encode and decode control signals communicated in parallel to the illuminators.

Another advantage of the above described parallel illuminating system is that the illuminators include LEDs with different light wavelength ranges wherein the central control system is able to switch on and switch off each illuminator independently on demand.

Another advantage of the above described parallel illuminating system is that regulating the plurality of illuminators is done automatically according to an image processing software program or hardware circuit configured to process captured images and provide control signals accordingly.

Another advantage of the above described parallel illuminating system is that transmitting control signal instructions over single power line 850 of FIG. 8A reduces the number of wires required at a multi camera sensor endoscope tip section, reduces the number of pins required in each illuminator to 2, hence, reduces the design complexity of the endoscope tip flexible PCB by reducing both the area and the number of PCB layers needed.

Another advantage of the above described parallel illuminating system is that the illuminators circuits' ASICs pin count is 2 (shown in FIG. 7 as 701 and 702), which allows manufacturing a small size ASIC. In a prior art endoscope tip comprising, say, 8 variable intensity LEDs—2 left side LEDs, 2 right side LEDs and 4 LEDs in the front, a total of 2+2+4+1 (ground)=9 wires are required. However, in the parallel illuminating system of the present specification only a total of 1+1 (ground)=2 wires are needed.

Another advantage of the above described parallel illuminating system is that one or more additional illuminators can be connected in parallel to one or more of illuminators connected in parallel to the single power line 850 of FIG. 8A.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

In addition, citation or identification of any reference in this application shall not be construed as an admission that such reference is available as prior art to the present invention.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

In case of conflict, the patent specification, including definitions, will prevail. In addition, the materials, methods, and examples are illustrative only and not intended to be limiting.

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description. While preferred embodiments of the present invention have been shown and described, it should be understood that various alternatives, substitutions, and equivalents can be used, and the present invention should only be limited by the claims and equivalents thereof.

The above examples are merely illustrative of the many applications of the system of the present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

I claim:

1. A video processing method for use in an endoscopy system, said endoscopy system having a plurality of daisy chained image sensors and a central control unit in data communication with said plurality of daisy chained image sensors, the method comprising:
   in a first of the plurality of daisy chained image sensors, generating video packets from images captured by a sensor array of the first of the plurality of daisy chained image sensors and storing said video packets in a self-packet buffer; and
   in said first of the plurality of daisy chained image sensors, interleaving video packets of said self-packet buffer and at least one void packet of a chained packet buffer and transmitting the interleaved video packets to another of the plurality of daisy chained image sensors;
   wherein said transmitting of the interleaved packets is performed with variable bitrates that depends on a position of the image sensors in said plurality of daisy chained image sensors, and wherein a data transfer rate of an image sensor is n+1 times the data transfer rate of a previous-in-chain image sensor, where n is the number of preceding image sensors in said plurality of daisy chained image sensors.

2. The video processing method according to claim 1, further comprising:
   in a second of the plurality of daisy chained image sensors, generating video packets from images captured by a sensor array of the second of the plurality of daisy chained image sensors and storing said video packets in a self-packet buffer;
   in said second of the plurality of daisy chained image sensors, storing in a chain packet buffer video packets received from another of the plurality of daisy chained image sensors; and
   in said second of the plurality of daisy chained image sensors, interleaving video packets of said self-packet buffer and said chained packet buffer and transmitting the interleaved video packets to another of the plurality of daisy chained image sensors.

3. The video processing method according to claim 1, further comprising:
   in a second of the plurality of daisy chained image sensors, generating video packets from images captured by a sensor array of the second of the plurality of daisy chained image sensors and storing said video packets in a self-packet buffer; and
   in said second of the plurality of daisy chained image sensors, interleaving video packets of said self-packet buffer and at least one void packet of a chained packet buffer and transmitting the interleaved video packets to another of the plurality of daisy chained image sensors.

4. The video processing method according to claim 1, further comprising:
   in a third of the plurality of daisy chained image sensors, generating video packets from images captured by a sensor array of the third of the plurality of daisy chained image sensors and storing said video packets in a self-packet buffer;
   in said third of the plurality of daisy chained image sensors, storing in a chain packet buffer video packets received from another of the plurality of daisy chained image sensors;
   in said third of the plurality of daisy chained image sensors, interleaving video packets of said self-packet buffer and said chained packet buffer and transmitting the interleaved video packets to a central control unit; and
   in said central control unit, de-interleaving said interleaved video packets and outputting de-interleaved and separated image frames captured by said plurality of daisy chained image sensors.

5. The video processing method according to claim 4, wherein the central control unit generates three separate and distinct video images from the interleaved video packets and transmits the three separate and distinct video images to three separate displays.

6. The video processing method according to claim 1, wherein said step of generating video packets from images further comprises compressing said video packets.

7. The video processing method according to claim 1, wherein an image capture frame rate of said plurality of daisy chained image sensors depends on a position of the image sensors in said plurality of daisy chained image sensors.

8. The video processing method according to claim 1, wherein an image capture frame rate of said plurality of daisy chained image sensors varies dynamically.

9. A video processing method for use in an endoscopy system, said endoscopy system having a plurality of daisy chained image sensors and a central control unit in data communication with said plurality of daisy chained image sensors, the method comprising:
- in a first of the plurality of daisy chained image sensors, generating video packets from images captured by a sensor array of the first of the plurality of daisy chained image sensors and storing said video packets in a self-packet buffer;
- in said first of the plurality of daisy chained image sensors, interleaving video packets of said self-packet buffer and at least one void packet of a chained packet buffer and transmitting the interleaved video packets to a second of the plurality of daisy chained image sensors;
- in the second of the plurality of daisy chained image sensors, generating video packets from images captured by a sensor array of the second of the plurality of daisy chained image sensors and storing said video packets in a self-packet buffer;
- in said second of the plurality of daisy chained image sensors, storing in a chain packet buffer video packets received from the first of the plurality of daisy chained image sensors; and
- in said second of the plurality of daisy chained image sensors, interleaving video packets of said self-packet buffer and at least one of said chained packet buffer and a void packet and transmitting the interleaved video packets to a third of the plurality of daisy chained image sensors;

wherein said transmitting of the interleaved packets is performed with variable bitrates that depends on a position of the image sensors in said plurality of daisy chained image sensors, and wherein a data transfer rate of an image sensor is n+1 times the data transfer rate of a previous-in-chain image sensor, where n is the number of preceding image sensors in said plurality of daisy chained image sensors.

10. The video processing method according to claim 9, wherein the central control unit generates three separate and distinct video images from the interleaved video packets and transmits the three separate and distinct video images to three separate displays.

11. The video processing method according to claim 9, wherein said steps of generating video packets from images further comprises compressing said video packets.

12. The video processing method according to claim 9, wherein an image capture frame rate of said plurality of daisy chained image sensors depends on a position of the image sensors in said plurality of daisy chained image sensors.

13. The video processing method according to claim 9, wherein an image capture frame rate of said plurality of daisy chained image sensors varies dynamically.

* * * * *